(12) United States Patent
Dvorak et al.

(10) Patent No.: US 8,977,421 B2
(45) Date of Patent: Mar. 10, 2015

(54) SYSTEM AND METHOD FOR DETERMINING A LUBRICANT DISCARD INTERVAL

(71) Applicant: Afton Chemical Corporation, Richmond, VA (US)

(72) Inventors: Todd M. Dvorak, Glen Allen, VA (US); Robert T. Dittmeier, Richmond, VA (US); Dewey P. Szemenyei, Suzhou (CN)

(73) Assignee: Afton Chemical Corporation, Richmond, VA (US)

( * ) Notice: Subject to any disclaimer, the term of this patent is extended or adjusted under 35 U.S.C. 154(b) by 0 days.

(21) Appl. No.: 14/448,168

(22) Filed: Jul. 31, 2014

(65) Prior Publication Data

US 2014/0343786 A1 Nov. 20, 2014

Related U.S. Application Data

(63) Continuation-in-part of application No. 13/363,433, filed on Feb. 1, 2012, now abandoned.

(51) Int. Cl.
*F01M 11/10* (2006.01)
*G01N 33/28* (2006.01)
*G06Q 10/00* (2012.01)

(52) U.S. Cl.
CPC .......... *F01M 11/10* (2013.01); *G01N 33/2888* (2013.01); *F01M 2011/1486* (2013.01); *F01M 2011/1466* (2013.01); *F01M 2011/1446* (2013.01); *F01M 2011/1473* (2013.01);
(Continued)

(58) Field of Classification Search
CPC .................. F01M 2011/14; F16N 2260/18

USPC ......................................................... 701/29.5
See application file for complete search history.

(56) References Cited

U.S. PATENT DOCUMENTS 5,592,395 A 1/1997 Braun et al.
5,750,887 A * 5/1998 Schricker ................... 73/114.55
5,914,890 A * 6/1999 Sarangapani et al. ........ 702/182
(Continued)

FOREIGN PATENT DOCUMENTS

EP 1229287 B1 10/2003
EP 1728983 A1 * 12/2006
(Continued)

OTHER PUBLICATIONS

Sinha, A.N. et al., "Assessment of useful life of lubricants using artificial neural network", Industrial Lubrication and Tribology, vol. 52 No. 3, 2000, pp. 105-109.*
(Continued)

*Primary Examiner* — Behrang Badii
*Assistant Examiner* — David Testardi
(74) *Attorney, Agent, or Firm* — Luedeka Neely Group, P.C.

(57) ABSTRACT

A system, a method and a computer program to determine the usability of a lubricant such as, e.g., engine oil, and when to replace the lubricant in a particular engine. The system, method, and computer program are further configured to generate a lubricant discard interval for each engine in, e.g., a company's fleet of vehicles. The system, method, and computer program are configured to generate lubricant discard interval schedule for each of the vehicles in the company's fleet based on the lubricant discard intervals.

11 Claims, 22 Drawing Sheets

(52) U.S. Cl.
CPC .... *F01M2011/1426* (2013.01); *F16N 2260/18* (2013.01); *F01M 2011/14* (2013.01); *G06Q 10/20* (2013.01)
USPC .................................................. 701/29.5

(56) References Cited

U.S. PATENT DOCUMENTS

| | | | |
|---|---|---|---|
| 5,964,318 A | 10/1999 | Boyle et al. | |
| 5,969,601 A * | 10/1999 | Sato et al. ................ | 340/450.3 |
| 5,987,976 A * | 11/1999 | Sarangapani .............. | 73/114.55 |
| 6,253,601 B1 * | 7/2001 | Wang et al. ............... | 73/114.55 |
| 6,283,082 B1 | 9/2001 | Gunshore et al. | |
| 6,324,899 B1 | 12/2001 | Discenzo | |
| 6,463,796 B1 * | 10/2002 | Van Mullekom et al. . | 73/114.55 |
| 6,741,938 B2 | 5/2004 | Berndorfer | |
| 6,776,024 B2 | 8/2004 | Jakoby | |
| 6,844,745 B1 | 1/2005 | Schachameyer et al. | |
| 6,859,039 B2 * | 2/2005 | Horie et al. .................. | 324/438 |
| 6,920,779 B2 * | 7/2005 | Carlstrom et al. .......... | 73/53.05 |
| 7,165,442 B2 | 1/2007 | Cryer et al. | |
| 7,581,434 B1 * | 9/2009 | Discenzo et al. ........... | 73/53.01 |
| 7,756,717 B2 * | 7/2010 | Dayal et al. .................... | 184/1.5 |
| 8,301,328 B2 * | 10/2012 | McAndrew et al. ......... | 701/29.1 |
| 8,707,773 B2 | 4/2014 | Blossfeld et al. | |
| 2004/0236706 A1 * | 11/2004 | Fitch et al. ................... | 705/400 |
| 2007/0074563 A1 | 4/2007 | Liu et al. | |
| 2009/0037206 A1 | 2/2009 | Byrne | |
| 2009/0139484 A1 | 6/2009 | Harris | |
| 2010/0299080 A1 * | 11/2010 | Willmann et al. .............. | 702/25 |
| 2011/0093157 A1 * | 4/2011 | Prabhakaran et al. ......... | 701/30 |
| 2013/0046433 A1 * | 2/2013 | Puckace et al. .............. | 701/29.5 |
| 2013/0197738 A1 * | 8/2013 | Dvorak et al. ............... | 701/29.5 |
| 2013/0197830 A1 * | 8/2013 | Dvorak et al. .................. | 702/46 |

FOREIGN PATENT DOCUMENTS

| | | | |
|---|---|---|---|
| EP | 2159387 A1 | 3/2010 | |
| JP | 03031746 A * | 2/1991 | ............ G01N 21/35 |
| JP | 09100712 A * | 4/1997 | ............ F01M 11/10 |
| JP | 09100712 A1 | 4/1997 | |
| JP | 2005016953 A1 | 1/2005 | |
| JP | 2005201392 A1 | 7/2005 | |
| KR | 1020020067995 A1 | 8/2002 | |

OTHER PUBLICATIONS

Robinson, Neil, "Monitoring oil degradation with infrared spectroscopy", Wear Check (Africa), Technical Bulletin 18, May 2000, 8 pages, downloaded from http://www.wearcheck.com/virtual_directories/Literature/Techdoc/WZA018.pdf.*

Felkel, Julia et al., "Characterization of gas engine oils by IR and Chemometrics", Poster Presentation: CAC 2008, 11th Intl. Conf. on Chemometrics in Analytical Chemistry, Jun. 30-Jul. 4, 2008, Montpellier, France, 6 pages.*

Greitzer, Frank L., "Life Extension Analysis and Prognostics Architectures", Laboratory Directed Research and Development Annual Report, Fisca Year 1999, PNNL-13203, published: 2000, pp. 85-88.*

Powell, Jay R., "Considerations in Applying Molecular Analysis of Different Fluids in a Condition Monitoring Program", Technology Showcase: Integrated Monitoring, Diagnostics and Failure Prevention, Proceedings of a Joint Conference, Mobile, Alabama, Apr. 22-26, 1996, 11 pages.*

Villar, Alberto et al., "Chemometric methods applied to the calibration of a Vis-NIR sensor for gas engine's condition monitoring", Analytica Chimica Acta, 705 (2011), pp. 174-181.*

Villar, A. et al., "Visible NIR on-line sensor for marine engine oil condition monitoring applying chemometric methods" , Proc. of SPIE vol. 7726, 77262F, Copyright 2010, 12 pages.*

JPO machine translation of JP 09-100712 (original JP document published Apr. 15, 1997).*

Amsoil Action News, "Oil Analysis is the Key to Safely Extending Drain Intervals and Equipment Life," Sep. 2003, p. 11, downloaded from http://bestsyntheticoil.com/action%20news/Sept2003/pg0011.pdf.

IDBS (web page), "Curve Fitting Best Practice," Google date: Feb. 23, 2009, 6 pages, downloaded from http://www.excelcurvefitting.com/pdfs/Curve%20Fitting%20Best%20Practive%20Part%203.pdf.

Real Statistics (web page), "Confidence and prediction intervals for forecast values," Google date: Feb. 1, 2001, 5 pages, downloaded from http://www.real-statistics.com/regression/confidence-and-prediction-intervals/.

Scarf, P.A., "A Framework for Condition Monitoring and Condition Based maintenance," Quality Technology & Quantitative Management, vol. 4, No. 2, 2007, pp. 301-312.

Scheller, Karl, "Statistical Trend Analysis of Wear Metal Concentration Measurements—Calculation of Significant Wear Metal Production Rates," Air Force Materials Laboratory Technical Report AFML-TR-79-4195, Dec. 1979, 67 pages, downloaded from http://www.dtic.mil/cgi-bin/GetTRDoc?Location=U2&doc=GetTRDoc.pdf&AD=ADB047220.

Toms, Larry A., "Adaptive Trend Analysis—A Simple Solution to Data Variability," 1998, AD-A347367, 6 pages, downloaded from www.dtic.mil/cgi-bin/GetTRDoc?AC=ADA347367.

* cited by examiner

GE ENGINES

| Parameter | Symbol | Critical<br>Shut Unit Down<br>CO Lube/Filters | Abnormal<br>Shop Unit<br>Immediately | Marginal<br>Shop Unit<br>Next Inspection | Problem |
|---|---|---|---|---|---|
| Copper | Cu | 125 ppm | 120 ppm | 95 ppm | Bearing, Rocker Arm Bushings, Lube oil Cooler |
| Lead | Pb | 50 ppm | 40 ppm | 35 ppm | Con-rod Bearings, Main Bearings |
| Iron | Fe | 85 ppm | 75 ppm | 65 ppm | Cylinder Liners |
| Chromium | Cr | 30 ppm | 25 ppm | 20 ppm | Piston Rings |
| Sodium | Na | 120 ppm | 85 ppm | 50 ppm | Coolant Leak |
| Boron | B | 50 ppm | 40 ppm | 25 ppm | Coolant Leak |
| Aluminum | Al | 20 ppm | 15 ppm | 10 ppm | Camshaft Bearings |
| Tin | Sn | 40 ppm | 30 ppm | 20 ppm | Bearings, Pistons |
| Phosphor | P | 120 ppm | 60 ppm | 40 ppm | Incorrect Lube Type, Fuel Dilution |
| Barium | Ba | 120 ppm | 60 ppm | 40 ppm | Incorrect Lube Type, Fuel Dilution |
| Silicon | Si | 15 ppm | 12 ppm | 10 ppm | Dirt Ingress, Water leak |
| Zinc | Zn | 30 ppm | 20 ppm | 15 ppm | Incorrect Lube Type |
| Nickel | Ni | 10 ppm | 5 ppm | 2 ppm | Exhaust valves |
| Calcium Low | Ca | 3000 ppm | 3500 ppm | 4000 ppm | Incorrect Lube Type, Fuel Dilution |
| P. Insolubles | - | 5% | 4% | 3% | Blowby, Timing |
| Water | - | 0.25% | 0.20% | 0.15% | Heads, Liners |
| Oxidation | - | 50 | 43 | 36 | Overheating, Defective lube oil cooler |
| Nitration | - | 80 | 70 | 56 | Blowby, Timing |
| Soot | - | 147 | 133 | 105 | Blowby, Timing |
| Fuel Dilution | - | 5.0% | 4.0% | 3.0% | Injectors, Fuel Lines |
| Viscosity High | - | 19.5 cst | 18.5 cst | 17.5 cst | Insolubles, Oxidation, Incorrect Lube Type |
| Viscosity Low | - | 12.5 cst | 13.0 cst | 13.5 cst | Fuel Dilution, Incorrect Lube Type |
| TAN | - | 5 | 4.6 | 4.1 | Acidity, Oxidation, Blowby |
| TBN | - | 4 | 5 | 6 | Depleted Lube Adpack |

FIG. 6

EMD ENGINES

700

| Parameter | Symbol | Critical Shut Unit Down CO Lube/Filters | Abnormal Shop Unit Immediately | Marginal Shop Unit Next Inspection | Problem |
|---|---|---|---|---|---|
| Silver | Ag | 3 ppm | 2 ppm | 1 ppm | Wrist Pin Bearings |
| Copper | Cu | 120 ppm | 90 ppm | 75 ppm | Thrust Washers, Bearings, Rocker Arm Bushings |
| Lead | Pb | 80 ppm | 75 ppm | 50 ppm | Con-rod Bearings, Main Bearings, , Wraist pin inserts |
| Iron | Fe | 125 ppm | 100 ppm | 75 ppm | Cylinder Liners, Con-rod, thrust bearing |
| Chromium | Cr | 20 ppm | 15 ppm | 8 ppm | Piston Rings |
| Sodium | Na | 120 ppm | 85 ppm | 50 ppm | Coolant Leak, External water leak, Preservative |
| Boron | B | 50 ppm | 40 ppm | 25 ppm | Coolant Leak |
| Aluminum | Al | 13 ppm | 10 ppm | 8 ppm | Crankshaft Oil Slinger |
| Silicon | Si | 20 ppm | 17 ppm | 15 ppm | Dirt Ingress, Coolant leak, External water leak |
| Zinc | Zn | 30 ppm | 20 ppm | 15 ppm | Incorrect Lube Type, Valve lifters |
| Nickel | Ni | 10 ppm | 5 ppm | 2 ppm | Exhaust valves |
| Tin | Sn | 40 ppm | 30 ppm | 20 ppm | Bearings, Pistons |
| Phosphor | P | 120 ppm | 60 ppm | 40 ppm | Incorrect Lube Type, Fuel Dilution |
| Barium | Ba | 120 ppm | 60 ppm | 40 ppm | Incorrect Lube Type, Fuel Dilution |
| Calcium Low | Ca | 3000 ppm | 3500 ppm | 4000 ppm | Incorrect Lube Type, Fuel Dilution |
| P. Insolubles | - | 6% | 5% | 4% | Blowby, Timing |
| Water | - | 0.25% | 0.20% | 0.15% | Heads, Liners |
| Oxidation | - | 35 | 28 | 25 | Overheating, Defective lube oil cooler |
| Nitration | - | 30 | 25 | 22 | Blowby, Timing |
| Soot | - | 175 | 161 | 133 | Injectors, Fuel Lines |
| Fuel Dilution | - | 5.0% | 4.0% | 3.0% | Insolubles, Oxidation, Incorrect Lube Type |
| Viscosity High | - | 19.5 cst | 18.5 cst | 17.5 cst | Fuel Dilution, Incorrect Lube Type |
| Viscosity Low | - | 11.0 cst | 11.5 cst | 12.0 cst | Acidity, Oxidation, Blowby |
| TAN | - | 4 | 3.6 | 3.4 | Depleted Lube Addpack |
| TBN | - | 5 | 6 | 7 | |

FIG. 7

| TAKEN | TESTED | Unit | Fe |
|---|---|---|---|
| 02/18/06 | 02/21/06 | 2248 | 2 |
| 03/06/06 | 03/08/06 | 2248 | 4 |
| 03/20/06 | 03/22/06 | 2248 | 6 |
| 04/04/06 | 04/05/06 | 2248 | 7 |
| 04/23/06 | 04/25/06 | 2248 | 10 |
| 05/07/06 | 05/09/06 | 2248 | 10 |
| 05/22/06 | 05/29/06 | 2248 | 11 |
| 06/09/06 | 06/09/06 | 2248 | 13 |
| 06/26/06 | 06/28/06 | 2248 | 15 |
| 07/10/06 | 07/11/06 | 2248 | 16 |
| 07/25/06 | 07/26/06 | 2248 | 18 |
| 08/13/06 | 08/15/06 | 2248 | 17 |
| 09/10/06 | 09/12/06 | 2248 | 6 |
| 09/22/06 | 09/27/06 | 2248 | 7 |
| 10/15/06 | 10/17/06 | 2248 | 8 |
| 10/29/06 | 10/31/06 | 2248 | 9 |
| 11/08/06 | 11/10/06 | 2248 | 8 |
| 11/20/06 | 11/21/06 | 2248 | 8 |
| 12/02/06 | 12/06/06 | 2248 | 8 |
| 12/16/06 | 12/19/06 | 2248 | 9 |
| 12/27/06 | 12/29/06 | 2248 | 10 |
| 01/07/07 | 01/15/07 | 2248 | 9 |
| 01/22/07 | 01/24/07 | 2248 | 11 |
| 02/13/07 | 02/16/07 | 2248 | 12 |
| 02/23/07 | 02/27/07 | 2248 | 4 |

SYSTEM AND METHOD FOR DETERMINING A LUBRICANT DISCARD INTERVAL

RELATED APPLICATION

This application is a continuation-in-part of application Ser. No. 13/363,433, filed Feb. 1, 2012, now pending.

FIELD OF THE DISCLOSURE

The present disclosure relates to a system, a method, and a computer program for determining usability of lubricants and when to replace the lubricants in, for example, an engine, a power transmission device, a turbine, a generator, a motor, or the like.

BACKGROUND AND SUMMARY OF THE DISCLOSURE

Engines (or motors) are designed to convert one form of energy (such as, for example, fuel combustion, electricity, nuclear reactions, and the like) to mechanical energy, such as, for example, mechanical motion. For instance, combustion engines convert fuel combustion energy to motion energy. These engines typically include one or more combustion chambers that contain and confine the combustion of a fuel (e.g., a fossil fuel), allowing the resultant high temperature and high pressure gases to expand and drive mechanical components such as, for example, pistons, turbine blades, or the like.

Internal combustion engines are typically used in vehicles, including, e.g., motorcycles, scooters, automobiles, boats, trucks, locomotives, watercraft, aircraft, ships, gas turbines, generators, heavy duty machinery, and the like. During operation of, for example, an internal combustion engine that comprises one or more pistons, a piston may be driven by expanding gases resulting from the combustion of the fuel in the chamber, causing the piston to move along a predetermined path for a predetermined distance along a length of the chamber. The piston may be connected to a crankshaft through a connecting rod to translate the movement of the piston to a rotation of the crankshaft. The engine may further include an intake valve or port and an exhaust valve or port. The engine may comprise any number of sets of pistons, connecting rods and chambers. The various moving parts of the engine cause friction, which results in the wear of the moving parts and diminished power output of the engine.

Most of the moving parts in the engine are made of metal. During operation, metal to metal contact of the moving parts causes wear on the moving parts. To minimize wear of the moving parts, and, therefore, to maximize engine durability and longevity, a lubricant (e.g., an engine oil) is used to lubricate the moving parts in the engine. The lubricant may also function to clean, inhibit corrosion, improve sealing, and cool the engine by carrying heat away from the moving parts. The lubricant reduces friction by, for example, creating a separating film between surfaces of adjacent moving parts to minimize direct contact between the surfaces, decreasing heat caused by the friction and reducing wear.

Most lubricants are made from a petroleum hydrocarbon derived from crude oil. Alternatively (or additionally), the lubricants may be made from synthetic materials, such as, e.g., synthetic esters, polyalphaolefins, and the like. Additives are added to the lubricant to maintain or improve certain properties of the lubricant. The additives may include, for example, detergents, dispersants, corrosion inhibitors, alkaline additives, and the like. One of the most important properties of lubricants is to maintain a lubricating film between the moving parts of the engine. Another important property of lubricants is its ability to neutralize acids.

In engines, the lubricants are exposed to the byproducts of internal combustion, including, for example, carbonaceous particles, metallic particles, and the like. During operation of the engine, the lubricants undergo both thermal and mechanical degradation, and contamination which impairs their function. Eventually the loss of performance may become significant enough to necessitate removal of the used lubricant and replacement with a fresh lubricant. Thus, time-based (e.g., 92 days, 184 days, 276 days, every 6 months, or the like) and/or distance-based (e.g., every three thousand miles, every five thousand miles, or the like) lubricant drainage intervals (LDIs) are typically used in determining when to replace the lubricants in an engine.

In the railroad industry, engine oil samples are typically taken from locomotive engines about every 2 to 3 weeks. These samples are then analyzed to identify problems, such as, e.g., coolant leaks, fuel dilution, metal wear, oil deterioration, improper oil in use, and the like. The railroads schedule oil change intervals based on, e.g., original equipment manufacturer (OEM) recommendations, operating history, and the like. Currently, a common industry practice for drain intervals is about every 184 days. However, this drain interval may be too long for some engines, such as, e.g., engines that are operated under severe conditions, or engines that are experiencing performance issues, or new engines that have just been placed into service and are susceptible to break-in wear. Further, the time between drain intervals may be shorter than optimal for some engines, such as, e.g., engines that are operated under ideally optimal conditions. Also, new engines may require more frequent oil changes than older engines.

In the trucking industry, for example, truck fleets have often utilized oil analysis to establish oil drain intervals for entire fleets. The oil drain intervals, however, are based on fleets rather than individual engines. Again, the established oil drain intervals may be too long for some engines, while shorter than necessary for others.

While lubricant drainage intervals are typically set based on the time in service or the distance that a vehicle has traveled, actual operating conditions and engine hours of operation may vary drastically for a give time in service or a distance traveled by a vehicle. Thus, fixed time/distance lubricant discard (or drain) intervals may result in the continued use of spent engine lubricant where an engine is operated under severe conditions or where the engine is not operating properly, which may result in poor fuel efficiency, costly maintenance, premature engine failure, and the like. The fixed time/distance lubricant discard intervals may also result in the premature, and therefore, inefficient discarding of engine lubricant that remains unspent at the discard interval, thereby increasing the amount of waste byproduct to be disposed of, as well as the costs associated with the replacement of the engine lubricant (including, e.g., the cost of the lubricant, the cost of labor to replace the lubricant, disposal costs, engine down time costs, and the like).

The engine lubricant may be considered to be spent when, for example, the properties of the engine lubricant have been degraded to a point where the engine lubricant ceases to properly lubricate the engine parts, inhibit corrosion, or the like.

Although it would seem ideal to analyze the condition of used oil from each piece of equipment and only change it when the analysis indicates it is close to the end of its useful life, there are other costs to consider in determining the most cost effective time to change oil. In their use, engines contribute to revenue production making it costly to take them out of service. As a consequence many maintenance tasks for equipment are preplanned and grouped together enabling these tasks to be performed during a planned shutdown of the equipment, or when many of the tasks can be performed simultaneously to minimize downtime. Equipment operators usually schedule maintenance to optimize overall cost. This means that to maximize production, individual maintenance tasks may be performed before they are actually needed.

Some maintenance tasks need to be performed more frequently than others. Preplanned maintenance is often based around a set of schedules. For example a fleet of trucks may have an A schedule every 30 days, a B schedule every 60 days, and a C Schedule every 120 days. A truck coming in for its first maintenance after 30 days would have all the services performed that are required in Schedule A. 30 days later it would have services A and B performed. 30 days after that (90 days cumulative) it would require the services in schedule A only. At 120 days of service it would require all the procedures in schedules A, B and C. The cycle would then be repeated.

If the fleet oil drain interval was scheduled for 30 days, and it was determined that a 45 day oil change interval would be safe, it is highly unlikely that taking these trucks out of service at 45 days only to change oil would be a cost effective undertaking. Moving the fleet to a 60 day oil change would be a practical endeavor, if that was determined to be a safe drain interval, because it would convert the oil change from a schedule A to a schedule B function, cut the oil change costs in half, and not result in any new out of service costs. If the oil change happened to be the only item in maintenance schedule A, this would result in a productivity improvement because the equipment would be taken out of service less frequently.

Because it is often difficult to predict how much useful life remains in a used oil, oil change intervals are frequently standardized across like pieces of equipment in a business unit. The oil change interval selection can be based on many different factors including the business unit's maintenance history with the specific equipment, the severity of service, the equipment manufacturer's recommendation, used oil analysis, etc. The oil change interval is usually chosen by what the business unit believes is the lowest overall cost in the trade-off between maintenance costs, repair costs, and downtime. Because no two units are identical, or used in identical service, the oil change interval is usually chosen to accommodate the most severe situation. This means that in a set of like engines, some engines that are milder or in milder service, and may be able to operate quite effectively on longer oil drain intervals.

A good example is railroad locomotives. These engines require safety inspections every 92 days. Oil changes used to be performed every 92 days to coincide with this out of service point. Many locomotive fleets have found that conditions are such that they can now change oil every 184 days. The next logical oil change interval increase would be to 276 days to coincide with a safety inspection. Some locomotives, particularly some GE FDL units under some operating conditions, cannot safely go for 276 days without an oil change. Thus, an unfulfilled need exists for a system and method to test used oil and predict at, for example, 150 days of service, based on the used oil analysis, which units should be changed at, e.g., 184 days and which units can safely continue to, e.g., 276 days without an oil change.

The foregoing oil change intervals contemplate removing all of the used oil from the engine and replacing all of the used oil with fresh oil on a selected oil change interval. Methods for predicting such interval typically use a linear regression model to determine one or more oil parameters that are predicted to be exceeded at some future point in time. While such models may be useful for such predictions, there continues to be a need for a more accurate prediction model for determining a lubricant discard (or drain interval).

In view of the foregoing and other needs, the disclosure provides a system, a method, and a computer program for predicting a lubricant drain interval in an engine based on a plurality of analysis parameter values measured in a plurality of samples of used engine lubricant taken from the engine over a period of time. The system includes a first input that receives the plurality of analysis parameter values and a plurality of historical analysis parameter values for the engine that are indicative of one or more characteristics of the used lubricant and stores the plurality of analysis parameter values and historical analysis parameter values in a memory of a processor. A second input that receives an analysis parameter threshold value for the used lubricant at the end of a service interval is stored in the memory of the processor. A determiner determines a future analysis parameter value for determining the lubricant drain interval by performing modeling of the plurality of analysis parameter values and historical analysis parameter values, and comparing the future analysis parameter value to the analysis parameter threshold value to determine whether or not the future analysis parameter value exceeds (or is less than) the analysis parameter threshold value at the end of the service interval in order to provide an output indicating the lubricant discard (or drain) interval (LDI) in an engine. The modeling performed by the determiner is selected from a partial least squares regression model, a neural network model, a general linear model regression model, and the like.

The determiner may be configured to generate the lubricant drain interval for the engine. The determiner may perform modeling on the historical analysis parameter value and said analysis parameter value to determine the future analysis parameter value. The modeling may comprise: a neural network analysis, a general linear model regression analysis, a generalized linear model regression analysis, a principle components regression analysis, a partial least squares analysis; and the like. The determiner may compare the future analysis parameter value to the analysis parameter threshold value. The determiner may generate the lubricant drain interval for the engine based on the comparison of the future analysis parameter value to the analysis parameter threshold value for the lubricant.

The first input may receive an additional analysis parameter value, and the determiner may perform a neural network analysis, a general linear model regression analysis, a generalized linear model regression analysis, a principle components regression analysis, a partial least squares analysis; and the like on the additional analysis parameter value. The analysis parameter value may include, for example, oil pressure, megawatt hours produced, locomotive unit age, a concentration of iron in the engine lubricant sample and the additional analysis parameter value may include, for example, a concentration of lead in the engine lubricant sample. The analysis parameter value and the additional analysis parameter value may be selected, for example, from iron, lead, tin, copper aluminum, boron, oxidation, nitration, potassium, silicon, sodium, soot, TBN, water, fuel, sludge, and insolubles in the engine lubricant sample.

The analysis parameter m is selected, for example, from a group of analysis parameters consisting of iron, lead, tin, copper aluminum, boron, oxidation, nitration, potassium, silicon, sodium, soot, water, fuel, sludge, insolubles, etc.

In addition to "used lubricant analysis parameters" described above, it may be beneficial to include "non used lubricant parameters" in the predictive model to ascertain the appropriate LDI and the need for unit servicing. Some examples of non used lubricant parameters that may be included in the model for determining the LDI and their potential effects on the determination of the LDI may include, but are not limited to: (1) oil pressure, wherein a decrease in oil pressure may indicate a water leak and an increase in oil pressure may indicate that the oil viscosity or soot content of the oil is increasing; (2) run time hours of an engine or unit wherein an increase or decrease in nm time hours may affect the "aging" rate of the lubricant in the unit or engine; (3) engine temperature, wherein high temperature engine conditions may affect the oxidation rate and volatile content losses of the lubricant. Volatile content losses may result in a lubricant viscosity increase due to thickening of the lubricant in the engine; (4) megawatt hours produced, wherein units that produce comparatively high levels of power may increase the "aging" rate of the lubricant in the crankcase, while production of low levels of power may decrease the "aging" rate of the lubricant: (5) total miles of the unit or engine between oil changes, wherein units having higher or lower cumulative miles between oil changes may affect the "aging" rate of the lubricant in the engine; and (6) the age of the engine or unit, wherein engines or units that are relatively new may exhibit a higher metal content in the lubricant due to mating parts wearing or "breaking in" during the early life of the engine or unit. All of the foregoing parameters and relationships may be linear, non-linear, or interactive with one or more used oil analysis parameters.

The method may further comprise predicting a probability when the future analysis parameter value will exceed the analysis parameter threshold value based on an equation derived from a logistic regression analysis or neural network (classification) analysis.

The present disclosure provides a system, a method, and a computer program for testing used oil and, using the methodology described herein, and predicting (or enabling a user to predict) at, for example, 150 days of service, based on the used oil analysis, which units in, e.g., a railroad locomotive fleet should be changed at, for example, 184 days and which can safely continue to, for example, 276 days without an oil change.

According to a further aspect of the disclosure, a method is provided for selecting a plurality of engines for an extended lubricant drain interval, the method comprising: retrieving lubricant discard interval data for a plurality of engines; categorizing the lubricant discard data into at least two categories, including an extended lubricant discard interval category and a normal lubricant discard interval category; and generating a lubricant discard interval schedule for the plurality of engines. The extended lubricant discard interval category may, for example, comprise 276 days and a normal lubricant discard interval category comprises 184 days.

According to a still further aspect of the disclosure, a method is provided for predicting a lubricant drain interval in an engine based on an analysis parameter value that is measured in a sample of engine lubricant taken from the engine, the method comprising: receiving at a first input the analysis parameter value; receiving at a second input an analysis parameter threshold value; and predicting a future analysis parameter value based on the analysis parameter value and the analysis parameter threshold value.

According to a still further aspect of the disclosure, a computer readable medium may be provided that comprises a computer program, as described herein, for carrying out the process described herein.

Additional features, advantages, and embodiments of the disclosure may be set forth or apparent from consideration of the detailed description and drawings. Moreover, it is noted that the foregoing summary of the disclosure and the following detailed description and drawings provide non-limiting examples of the disclosure, which are intended to provide explanation without limiting the scope of the disclosure as claimed.

BRIEF DESCRIPTION OF THE DRAWINGS

The accompanying drawings, which are included to provide a further understanding of the disclosure, are incorporated in and constitute a part of this specification, illustrate embodiments of the disclosure and together with the detailed description serve to explain the principles of the disclosure. No attempt is made to show structural details of the disclosure in more detail than may be necessary for a fundamental understanding of the disclosure and the various ways in which it may be practiced. In the drawings:

FIG. 6 shows an example of General Electric (GE) OEM recommendations for a GE locomotive engine;

FIG. 7 shows an example of Electro-Motive Diesel (EMD) OEM recommendations for an EMD locomotive engine;

FIG. 8 shows an example of historical data that may be retrieved from a data storage for a particular engine;

Figure 1:
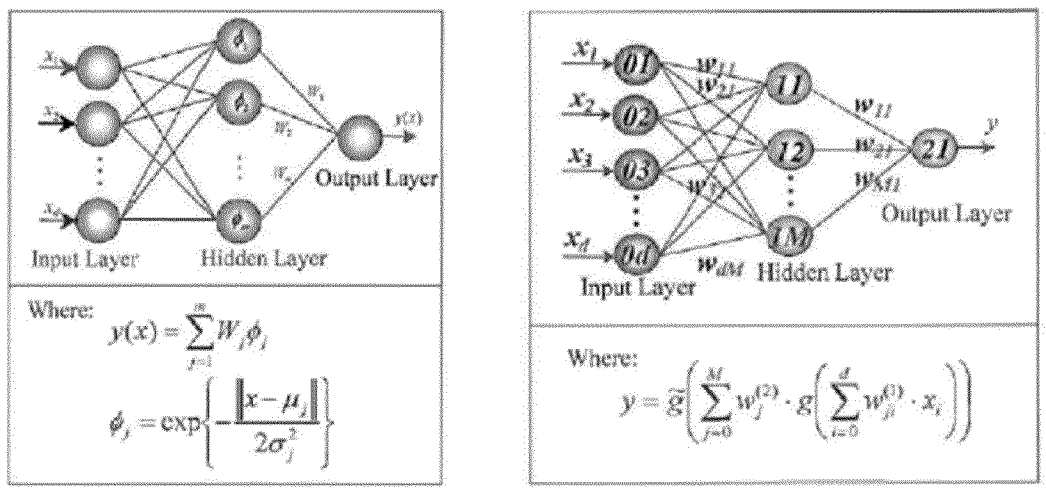
FIG. 1 is a graphical representation of a multilayer perceptron and radial basis neural network used for analysis according to an embodiment of the disclosure.

The present disclosure is further described in the detailed description that follows.

DETAILED DESCRIPTION OF THE DISCLOSURE

The disclosure and the various features and advantageous details thereof are explained more fully with reference to the non-limiting embodiments and examples that are described and/or illustrated in the accompanying drawings and detailed in the following description. It is noted that the features illustrated in the drawings and attachment are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure. Moreover, it is noted that like reference numerals represent similar parts throughout the several views of the drawings.

"Used lubricant" as used in the disclosure refers to lubricant from an engine that has been operating for a period of time. The used lubricant may be from an initial charge of lubricant at a service interval or may be lubricant that is supplemented between service intervals by fresh lubricant.

A "computer," as used in this disclosure, means any machine, device, circuit, component, or module, or any system of machines, devices, circuits, components, modules, or the like, which are capable of manipulating data according to one or more instructions, such as, for example, without limitation, a processor, a microprocessor, a central processing unit, a general purpose computer, a super computer, a personal computer, a laptop computer, a palmtop computer, a notebook computer, a cloud computer, a desktop computer, a workstation computer, a server, or the like, or an array of processors, microprocessors, central processing units, general purpose computers, super computers, personal computers, laptop computers, palmtop computers, notebook computers, desktop computers, workstation computers, servers, or the like.

A "server," as used in this disclosure, means any combination of software and/or hardware, including at least one application and/or at least one computer to perform services for connected clients as part of a client-server architecture. The at least one server application may include, but is not limited to, for example, an application program that can accept connections to service requests from clients by sending back responses to the clients. The server may be configured to run the at least one application, often under heavy workloads, unattended, for extended periods of time with minimal human direction. The server may include a plurality of computers configured, with the at least one application being divided among the computers depending upon the workload. For example, under light loading, the at least one application can run on a single computer. However, under heavy loading, multiple computers may be required to run the at least one application. The server, or any if its computers, may also be used as a workstation.

"Linear regression," as used in this disclosure, means any known linear regression methodology known by those skilled in the art, including general linear models (GLM) such as, for example, polynomial expressions that may be restricted to a class of problems that satisfy a set of requirements. These requirements pertain to the model error. The model error is the difference between the observed value and the predicted value. The investigation of the model error is a key factor for evaluating model adequacy. The required assumptions for general linear models include: the errors have a mean of zero; the errors are uncorrelated; the errors are normally distributed; and the errors have a constant variance. If any of the foregoing assumptions are violated, then it is generally required to apply some sort of transformation, add more variables to accommodate systemic sources of variance, or apply another type of modeling method such as a non-linear type of modeling approach.

"Linear regression," as used in this disclosure, may include a "generalized linear model" (GLZ). A GLZ has two key features that distinguish it from the GLM method. It includes a link and a distribution function. The link is a transformation function such as an identity, a power, or log. The distribution function pertains to the error component. In GLM, the errors are normally distributed. With GLZ, the errors can be specified as normal or from one of the exponential family of distributions. Some examples include the Poisson, binomial, gamma, and inverse Gaussian. Due to the link and distribution function, this type of modeling approach may be referred to as a "nonlinear" type of modeling.

"Logistic regression" is a unique modeling approach for binary or dichotomous type response data. Logistic regression may be applied to problems that have pass/fail {0, 1}data. The two unique features for the logistic regression model include: the conditional mean of the regression equation must be formulated to be bounded between 0 and 1; and the binomial distribution describes the distribution of the errors. The predicted value for the logistic model can be expressed as the logged odds or probability of a pass/fail for a unique set of conditions of the independent (x) variables.

In the case of the used lubricant (or oil) analysis, logistic regression models may be used to predict the probability that a critical threshold for a used lubricant parameter will be exceeded. If the predicted probability is high that a critical lubricant life parameter will be exceeded, then the conclusion will be that the lubricant drain interval should not be extended.

Other modeling techniques such as Partial Least Squares. Principal Components Regression, General Linear Models. Generalized Linear Models, Neural Networks, and the like may be applied to predict/forecast the value for a set of used lubricant critical parameter(s). Alternatively, a discriminate analysis can also be applied to identify the variables/attributes that separate the used lubricant data into two different groups. The first and second groups in the discriminate analysis correspond to the conditions that can and cannot lead to the extension of the lubricant drain interval.

A "neural network" may be an effective nonlinear and assumption free type of modeling approach. Two common architectures of Neural Networks include, for example, Multi-Layer Perceptron (MLP) and Radial Basis Function (RBF). The output of the RBF network is a function of the network weights, radial distances, and sigma width parameter. The output of the MLP is based on the weighted sum of the inputs and an activation function. The sigmoid is the general type of activation function form of a neural network is shown in FIG. 1. In FIG. 1, the variables x1 . . . xd are predictor variables, w1 . . . wd (or dM) and w11 . . . wM1 are weighting values, and y is the output.

For example, the response parameter (y) data may be linear or nonlinear related to the predictor (x) variables. As shown in the TBN plot in FIG. 11 for unit Locomotive Unit 2248, the relationship between the predictor (x), oil age, and the response parameter (y) TBN corresponds with a non-linear decreasing trend. In this example, it may be advantageous to utilize a higher order polynomial expression, neural network (NN), natural log transform of oil age days to better characterize the underlying relationship between TBN and oil age.

Figure 9:
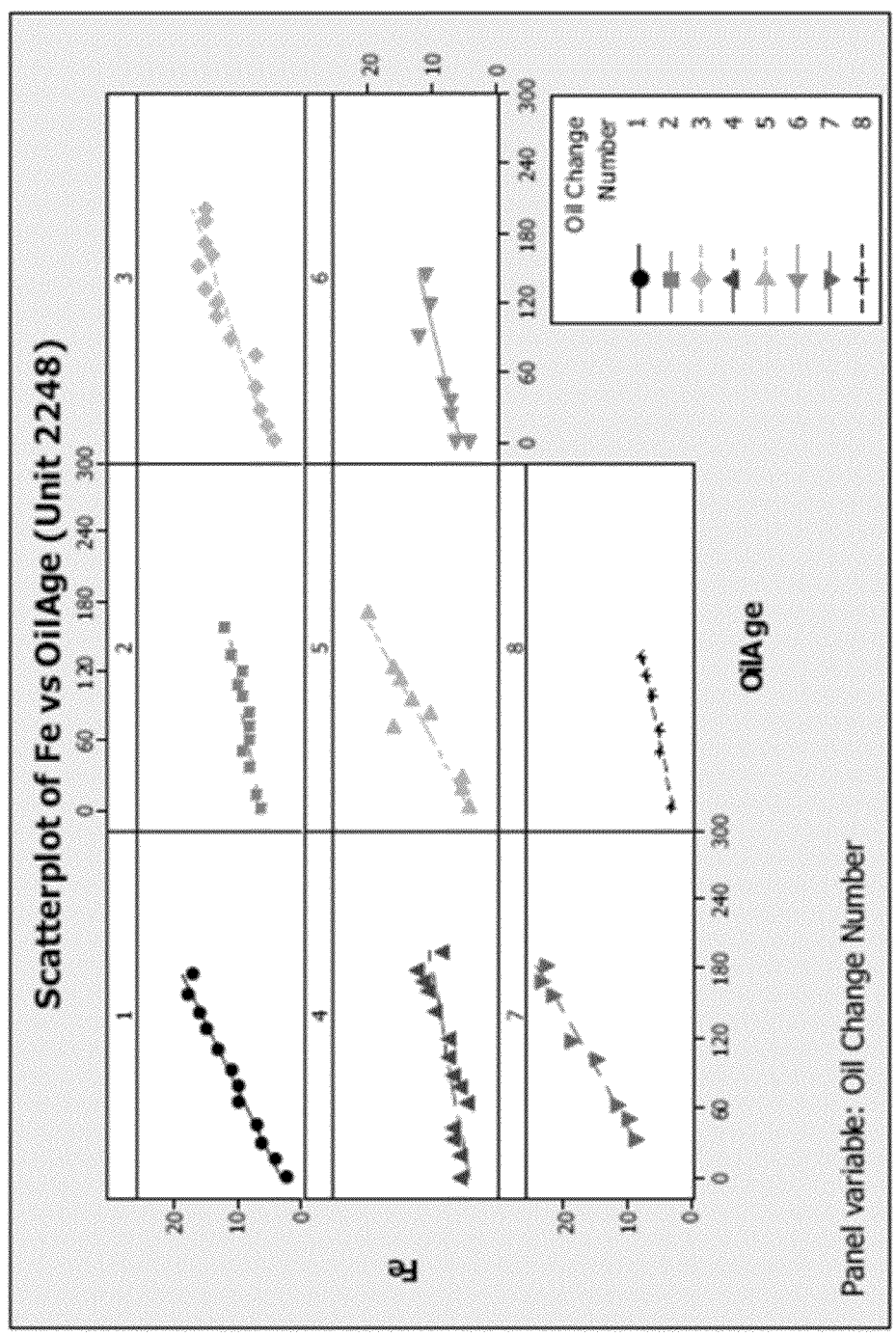
FIG. 9 shows an example of eight scatter plot charts of iron (Fe) versus oil-age for a locomotive unit.

In FIG. 9, the relationship between the response parameter (y) and oil age may be linear. As shown in the Fe (iron) plot for unit Locomotive Unit 2248, the relationship between the predictor (x), oil age, and the response parameter (y) Fe (iron) tends to exhibit a linear increasing trend. As such, this data may be expressed with a linear polynomial function.

A "database," as used in this disclosure, means any combination of software and/or hardware, including at least one application and/or at least one computer. The database may include a structured collection of records or data organized according to a database model, such as, for example, but not limited to at least one of a relational model, a hierarchical model, a network model or the like. The database may include a database management system application (DBMS) as is known in the art. The at least one application may include, but is not limited to, for example, an application program that can accept connections to service requests from clients by sending back responses to the clients. The database may be configured to run the at least one application, often under heavy workloads, unattended, for extended periods of time with minimal human direction.

A "communication link," as used in this disclosure, means a wired and/or wireless medium that conveys data or information between at least two points. The wired or wireless medium may include, for example, a metallic conductor link, a radio frequency (RF) communication link, an Infrared (IR) communication link, an optical communication link, or the like, without limitation. The RF communication link may include, for example, WiFi, WiMAX, IEEE 802.11, DECT, 0G, 1G, 2G, 3G or 4G cellular standards, Bluetooth, and the like.

A "network," as used in this disclosure means, but is not limited to, for example, at least one of a local area network (LAN), a wide area network (WAN), a metropolitan area network (MAN), a personal area network (PAN), a campus area network, a corporate area network, a global area network (GAN), a broadband area network (BAN), a cellular network, the Internet, or the like, or any combination of the foregoing, any of which may be configured to communicate data via a wireless and/or a wired communication medium. These networks may run a variety of protocols not limited to TCP/IP, IRC or HTTP.

The terms "including," "comprising," and variations thereof as used in this disclosure, mean "including, but not limited to", unless expressly specified otherwise.

The terms "a," "an," and "the," as used in this disclosure, means "one or more", unless expressly specified otherwise.

Devices that are in communication with each other need not be in continuous communication with each other, unless expressly specified otherwise. In addition, devices that are in communication with each other may communicate directly or indirectly through one or more intermediaries.

Although process steps, method steps, algorithms, or the like, may be described in a sequential order, such processes, methods, and algorithms may be configured to work in alternate orders. In other words, any sequence or order of steps that may be described does not necessarily indicate a requirement that the steps be performed in that order. The steps of the processes, methods, or algorithms described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

A "computer-readable medium," as used in this disclosure, means any medium that participates in providing data (for example, instructions) which may be read by a computer. Such a medium may take many forms, including non-volatile media, volatile media, and transmission media. Non-volatile media may include, for example, optical or magnetic disks and other persistent memory. Volatile media may include dynamic random access memory (DRAM). Transmission media may include coaxial cables, copper wire, and fiber optics, including the wires that comprise a system bus coupled to the processor. Transmission media may include or convey acoustic waves, light waves and electromagnetic emissions, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, a carrier wave as described hereinafter, or any other medium from which a computer can read. The computer-readable medium may include a "Cloud," which includes a distribution of files across multiple (e.g., thousands of) memory caches on multiple (e.g., thousands of) computers.

Various forms of computer readable media may be involved in carrying sequences of instructions to a computer. For example, sequences of instruction (i) may be delivered from a RAM to a processor, (ii) may be carried over a wireless transmission medium, and/or (iii) may be formatted according to numerous formats, standards or protocols, including, for example, WiFi, WiMAX, IEEE 802.11, DECT, 0G, 1G, 2G, 3G or 4G cellular standards, Bluetooth, or the like.

Figure 2A:
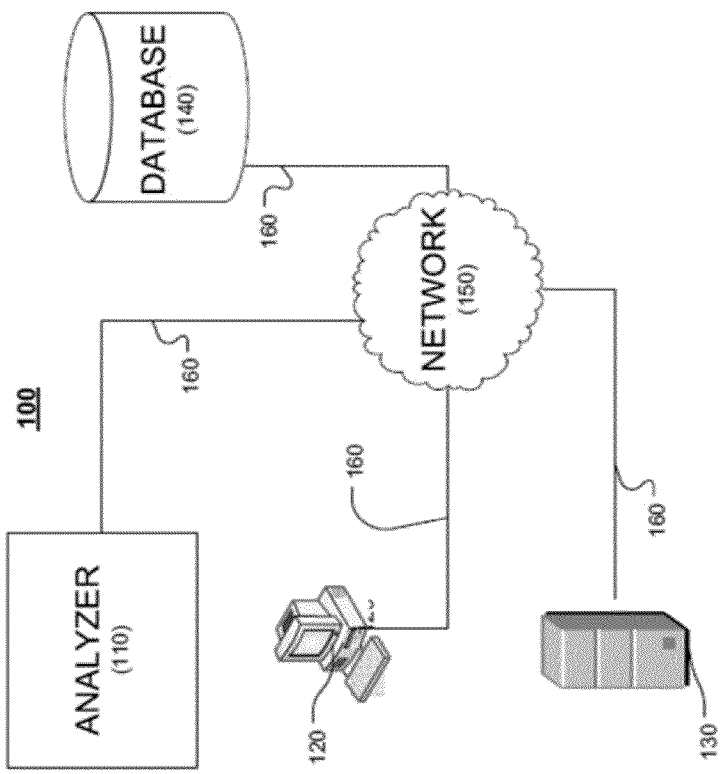
FIG. 2A shows an example of a system that determines the usability of a lubricant and when to replace the lubricant.

FIG. 2A shows an example of a system 100 that determines the usability of a lubricant and when to replace the lubricant in, for example, an engine. The system 100 comprises an analyzer 110, a computer 120, a server 130, and a database 140, all of which may be linked through a network 150 via communication links 160 or directly via the communication links 160. The analyzer 110 may be located on (or in) an engine, in an engine compartment of a vehicle, in a building, or the like. The computer 120 may be located at, e.g., a customer site, such as, e.g., a customer shop, a customer building, or the like. The server 130 and/or database 140 may be located at a product provider site, such as, e.g., an engine lubricant distributor or supplier, an engine lubricant retailer, or the like.

The analyzer 110 may include, e.g., a spectral analyzer, a viscosity analyzer, an acid analyzer, a solids analyzer, a flashpoint analyzer, an oxidation analyzer, a nitration analyzer, and the like. The analyzer 110 is configured to receive a sample of an engine lubricant that has been taken from a particular engine and analyze the sample to identify and measure one or more analysis parameters. For instance, the spectral analyzer 110 may perform spectral analysis of the lubricant sample to determine the levels (e.g., in parts per million (ppm)) of analysis parameters. The analysis parameters (AP) may include, e.g., wear metals, contaminants, additives, and the like, that may be present in the lubricant. The analysis parameters may also include an indication and concentration of engine coolant in the lubricant. The spectral analyzer may include, e.g., a Rotrode Emission Spectrometer, an Inductively Coupled Plasma Spectrometer, or the like. The wear metals that may be identified and measured include, e.g., aluminum, antimony, chromium, copper, iron, lead, nickel, silver, tin, titanium, zinc, and the like. The additives that may be identified and measured include, e.g., antimony, boron, calcium, copper, magnesium, molybdenum, phosphorus, potassium, silicon, sodium, zinc, and the like. The contaminants that may be identified and measured include, e.g., zinc, boron, potassium, silicon, sodium, soot, water, fuel, sludge, insolubles, and the like. The oxidation and nitration analyzers may provide information concerning degradation of the lubricant by measuring oxidation and nitration, respectively.

The viscosity analyzer may include, e.g., a viscometer that performs viscosity analysis to determine the effective grade of the lubricant. The viscosity analyzer may measure the lubricant at a temperature of, e.g. $-35°$ C., $-20°$ C., $0°$ C., $40°$ C., $100°$ C., or any other temperature, as is known in the art. The viscosity analyzer may measure the effective viscosity of the lubricant by, e.g., measuring the time that it takes the lubricant to flow between two sensors that are provide on a conduit (e.g., a glass tube, or the like) that is maintained at a constant temperature. Alternatively (or additionally) the viscosity analyzer may measure, e.g., high temperature, high shear, dynamic, kinematic, and the like.

An acid analyzer may measure the lubricant's Total Base Number (TBN) by, e.g., mixing the lubricant with a diluent and titrating the mixture with, e.g., alcohol-Hydrochloric acid (HCl) solution until all of the alkaline constituents that are present in the lubricant are neutralized. The acid analyzer may additionally (or alternatively) measure the lubricant's Total Acid Number (TAN). In this regard, the acid analyzer may, e.g., mix the engine lubricant with a diluent and, then, titrate the mixture with, e.g., alcohol-potassium hydroxide (KOH) until all of the acids present in the engine lubricant have been neutralized. The TAN or TBN results may be reported in milligrams of, e.g., KOH or HCl per gram of engine lubricant.

The solids analyzer may perform an analysis of the solids in the lubricant to identify the particular solids and the concentration of the solids in the lubricant. The solids analyzer may include, e.g., a laser-based particle counter, infrared analyzer, or the like, that detects and measures the concentration of particles in a sample of lubricant.

The flashpoint analyzer may analyze the lubricant to determine the temperature at which the vapors from the lubricant ignite. For instance, the flashpoint analyzer may slowly heat a sample of lubricant, keeping accurate measurements of the temperature of the sample. When the evaporated gases ignite or become ignitable, the temperature of the sample may be recorded as the flash point temperature of the particular lubricant sample.

The analyzer 110 may include a transceiver (not shown) that is configured to send and receive data and instructions over the communication link 160. For instance, the analyzer 110 may be configured to send data from the engine or the engine compartment of the vehicle to the customer computer 120 and/or the server 130 or database 140. The analyzer 110 may be configured to directly sample an engine lubricant in an engine and provide analysis data in substantial real-time, which may be sent to the customer computer 120 and/or the server 130 (or database 140).

Alternatively, the analyzer 110 may be located at a remote laboratory, where samples (e.g., 4 oz, 8 oz, or the like) of engine lubricant may be received at the laboratory for testing via messenger, mail, or the like. The results of the analysis may be sent by the analyzer 110 to the customer computer 120 and/or the server 130 via the communication links 160. For instance, after a sample of the engine lubricant has been analyzed by the analyzer 110, the engine lubricant analysis results may be sent to the database 140, where the results may be associated with and stored in, e.g., a database record (or file) that is associated with a particular engine, a particular engine type, a particular vehicle, a particular engine manufacturer, a particular vehicle manufacturer, a particular entity (e.g., a person, a company, an institution, or the like), or the like. The database record may include historical information, including past lubricant analysis results for the associated engine and/or vehicle. It is noted that the database 140 may be located internally in the server 130.

Figure 2B:
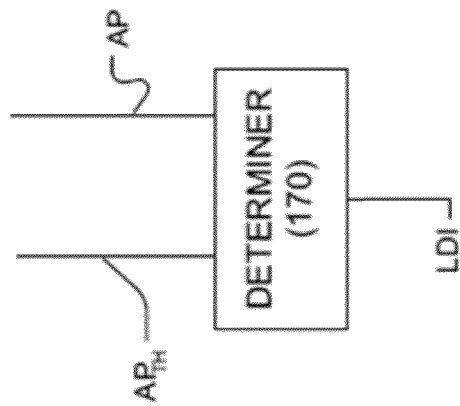
FIG. 2B shows a representation of a determiner module that may be included in the system of FIG. 2A.

FIG. 2B shows a representation of a determiner module 170 that may be included in the server 130 to carry out an aspect of the disclosure. The determiner 170 may include software and/or hardware. The determiner 170 may include a central processing unit (CPU) and a memory. The determiner 170 is configured to receive and compare a measured analysis parameter value AP to an analysis parameter threshold value $AP_{TH}$. The determiner 170 determines a lubricant discard (or drain) interval (LDI) based on the comparison of the measured analysis parameter value AP to the analysis parameter threshold value $AP_{TH}$. The determiner 170 may provide an output that indicates whether the LDI interval may be extended, or not, or whether it needs to be shortened.

According to an embodiment of the disclosure, the determiner 170 is configured to receive and compare each of a plurality of measured analysis parameter values, $AP_1, \ldots, AP_n$, to the analysis parameter threshold value $AP_{TH}$ for a particular analysis parameter in a particular engine, where the analysis parameter values $AP_1, \ldots, AP_n$ include the measured levels or concentrations of the particular analysis parameter AP in n samples of engine lubricant that were taken over n separate dates, where n is a positive integer that is greater than, or equal to 1. The determiner 170 may include artificial intelligence, such as, e.g., a neural network, fuzzy logic, or the like, that performs linear regression, non-linear regression, logistic regression, or the like, on the plurality of analysis parameter values $AP_1, \ldots, AP_n$ for each analysis parameter. The determiner 170 may implement, e.g., "if-then" methodologies to predict future AP values. For example, the determiner 170 may determine an LDI for a given engine by determining if AP(soot)>45 at day 150, then the determiner 170 may predict that the soot critical value will be exceeded at day 276; or, if AP(VIS100C)>16.5 and AP(TAN)>3.8 at day 150, then the critical values for TAN or VIS100C will be exceeded, thereby making it necessary to set the LDI at a point sooner than 276 days, such as, e.g., at 184 days. The determiner 170 is configured to monitor and predict when an AP value (e.g., level, concentration, or the like) of the analysis parameter will likely exceed the associated threshold value $AP_{TH}$ by using, e.g., linear regression, non-linear regression, logistic regression, or the like.

The determiner 170 is configured to repeat the process for m different analysis parameters, where in is equal to or greater than 1, and where in corresponds to the number of different analysis parameters that are identified and measured in n samples of engine lubricant that are taken from and analyzed for a particular engine. That is, the determiner 170 performs, e.g., a linear regression, Neural Network Analysis, or Partial Least Squares Analysis, and the like for each of the values $AP(1)_1, \ldots, AP(1)_m, \ldots, AP(m)_1, \ldots, AP(m)_n$, while comparing each of the values $AP(1)_1, \ldots, AP(1)_m, \ldots, AP(m)_1, \ldots, AP(m)_n$ to respective threshold values $AP(1)_{TH} \ldots AP(m)_{TH}$. As noted earlier, the analysis parameter value AP may include, for example, a level, an amount, a concentration, or the like, of a wear metal, an additive, a contaminant, or the like, in a sample of engine lubricant. The determiner 170 predicts an occurrence (e.g., a time, a day, a date, or the like) when a future analysis parameter value $AP_{n+1}$ is expected to exceed (or fall under) the associated threshold value $AP_{TH}$ for the associated analysis parameter. The determiner 170 may then set the LDI based on the predicted occurrence. For instance, the determiner 170 may set an LDI on a date that is well before, or just prior to when the future value $AP_{n+1}$ is expected to exceed (or fall under) the associated threshold value $AP_{TH}$.

The determiner 170 may be configured to perform different prediction methodologies for different analysis parameters. For instance, the determiner 170 may implement linear extrapolation to predict future values for iron or soot, but implement logarithmic prediction (non-linear prediction) to predict future values for lead.

Figure 3:
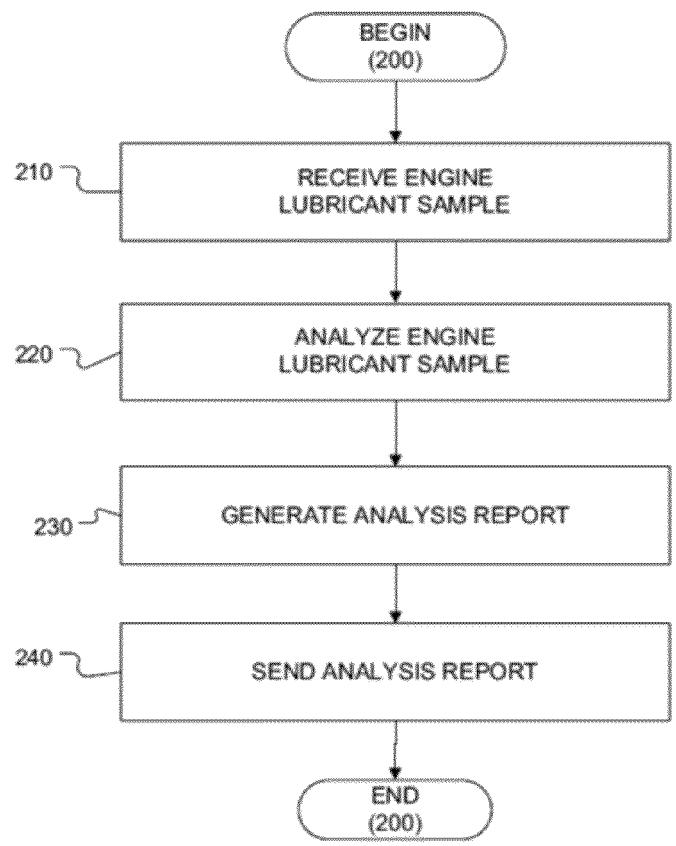
FIG. 3 shows an example of a lubricant analysis process for analyzing a sample of an engine lubricant.

FIG. 3 shows an example of a lubricant analysis process 200 for analyzing a sample of an engine lubricant. Referring to FIGS. 2A-2B and 3, the process 200 begins when a sample of engine lubricant is received at the analyzer 110 from a source (Step 210). The source may include, e.g., an engine, an individual, a company (e.g., railroad company, trucking company, shipping company, rental car company, or the like), an institution (e.g., a school, a hospital, or the like), an agency (e.g., a government agency, or the like), or the like. In the instance where the analyzer 110 (shown in FIG. 2A) is located on (or in) the engine, or in the engine compartment near the engine, the source may be the engine itself, and the analyzer 110 may be placed, e.g., in the lubricant flow path, between the engine and an external lubricant filter (e.g., an engine oil filter) or an external lubricant cooler (e.g., an engine oil cooler).

After the sample of the engine lubricant is received (Step 210) from a particular engine, the lubricant sample may be analyzed by the analyzer 110 to identify and measure the types and concentrations of the wear metals, the additives, the contaminants, and the like, that are present in the lubricant. The analyzer 110 may further measure TBN, TAN, viscosity, flashpoint, and the like, of the lubricant.

The results of the analysis may be compiled and reproduced in an analysis report for the analyzed sample of engine lubricant (Step 230). The analysis report may then be sent to the customer computer 120 and/or the server 130 (Step 240). The report may be sent to the database 140, where the report may be associated with and stored in a record for the particular engine. Alternatively, the analysis report may be displayed directly on, e.g., an on-board-display (not shown) of a vehicle (Step 240). The lubricant analysis report may be include, e.g., raw data, tabulated data, or the like, for the identified and measured analysis parameters, including, e.g., wear metals, additives, contaminants, TBN, TAN, viscosity, flashpoint, and the like. The lubricant analysis report may be generated and produced in human readable form (e.g., a printout, a display, an audio file, a video file, a multimedia file, or the like), so as to be readable by a human, or the report may be provided in a machine-readable format, so that the report may be received and processed by the customer computer 120, the server 130, and/or the database 140 without any human intervention.

According to an aspect of the disclosure, a computer readable medium is provided that contains a computer program, which when executed in, for example, the analyzer 110, which may include a computer (not shown), causes the process 200 in FIG. 3 to be carried out. The computer program may be tangibly embodied in the computer readable medium, which may comprise a code segment or a code section for each of the steps 210 through 240.

Figure 4:
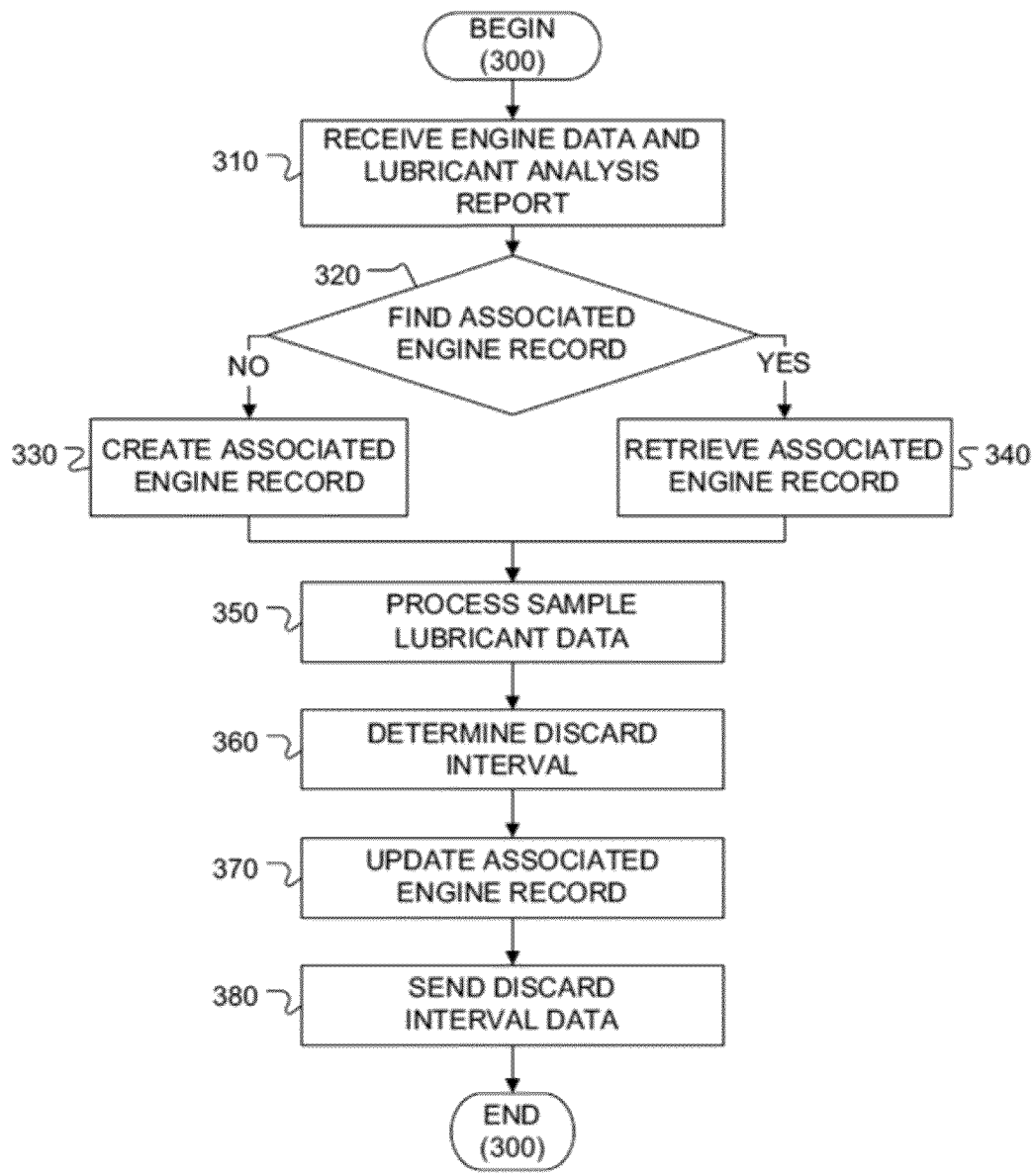
FIG. 4 shows an example of an engine lubricant discard interval determination process for determining the usability of an engine lubricant and establishing an engine lubricant discard interval for a particular engine.

FIG. 4 shows an example of an engine lubricant discard interval determination process 300 for determining the usability of an engine lubricant and establishing an engine lubricant discard interval for a particular engine.

According to an embodiment of the disclosure, the process 300 may be carried out by the customer computer 120 or the server 130. The results of the process 300 may be stored in the database 140. Alternatively, according to another embodiment of the disclosure, the process 300 may be carried out in its entirety by the analyzer 110.

Referring to FIG. 4, initially, engine data and a lubricant analysis report are received by, e.g., the server 130 (or customer computer 120) for a particular engine or a particular vehicle (Step 310). The engine data may include, e.g., the year in which the engine was manufactured, the engine type, the engine manufacturer, the engine displacement, the place of manufacture of the engine, the engine serial number, the vehicle serial number in which the engine is installed, and the like. The lubricant analysis report may be received from, e.g., the analyzer 110 (Step 240 in FIG. 3) and the report may include analysis parameter values $AP(1)_n, \ldots, AP(m)_n$.

The server 130 may query its internal data storage 135 (shown in FIG. 5) or the database 140 to determine if a record exists for the particular engine identified by the received engine data (Step 320). If it is determined that a record does exist for the particular engine (YES at Step 320), then the identified record is retrieved from storage 135 (or 140) (Step 340). The retrieved record may include a plurality of historical values for each of the measured analysis parameters, e.g., values $AP(1)_1, \ldots, AP(1)_{n-1}, \ldots, AP(m)_1, \ldots, AP(m)_{n-1}$.

If it is determined that record does not exist for the particular engine (NO at Step 320), then a record is created in the local data storage 135 (FIG. 5) and/or the database 140 (FIG. 2A) (Step 330). The created record may include a plurality of fields for the particular engine, including, e.g., a customer name (e.g., a railroad company, a trucking company, a shipping company, or the like), a customer address (e.g., an email address, a geographic address, a telephone number, a point of contact name, or the like), the year in which the engine was manufactured, the engine type, the engine manufacturer, the engine displacement, the place of manufacture of the engine, the engine serial number, the last service date for the engine, the details of the last service, the date that the engine was put into operation, the number of hours on the engine, the number of miles on the engine, the vehicle serial number in which the engine is installed, and the like. The fields of the record may be populated with the data received in the engine data (Step 310). The created record may further include OEM recommendations (e.g., recommendations 600, 700, shown in FIGS. 6, 7, respectively), industry recommendations, trade group recommendations, standards body recommendations, individual recommendations, or the like, which may include threshold values for one or more analysis parameters, $AP_{TH}(1), \ldots, AP_{TH}(m)$.

The received lubricant sample data may be processed by the server 130 (e.g., the determiner 170, shown in FIG. 2B) and the analysis parameter values for the particular engine, $AP(1)_n, \ldots, AP(m)_n$, along with the historical values, $AP(1)_1, \ldots, AP(1)_{n-1}, \ldots, AP(m)_1, \ldots, AP(m)_{n-1}$, may be compared against the associated analysis parameter threshold values $AP_{TH}(1), \ldots, AP_{TH}(m)$ (Step 350). Further, a lubricant discard interval LDI may be determined by performing an analysis on the values $AP(1)_1 \ldots, AP(1)_n, \ldots, AP(m)_1, \ldots, AP(m)_n$, to predict when a value of the future analysis parameter values $AP(1)_{n+1}, \ldots, AP(m)_{n+1}$ will exceed (or fall under) an associated threshold value $AP_{TH}(1) \ldots AP_{TH}(m)$ (Step 360). The LDI may include, e.g., a time, a day, a number of days, a date, a number of engine hours, or the like. The record for the particular engine may be updated to include the LDI information and the received analysis parameter values $AP(1)_n, \ldots, AP(m)_n$, as well as the predicted values $AP(1)_{n+1}, \ldots, AP(m)_{n+1}$ (Step 370). The generated LDI data may be sent to the customer computer 120 (or the server 130) and/or the database 140 (Step 380).

According to an aspect of the disclosure, a computer readable medium is provided that contains a computer program, which when executed in, for example, the server 130 (or the computer 120), causes the process 300 in FIG. 4 to be carried out. The computer program may be tangibly embodied in the computer readable medium which may comprise a code segment or a code section for each of the steps 310 through 380.

Figure 5:
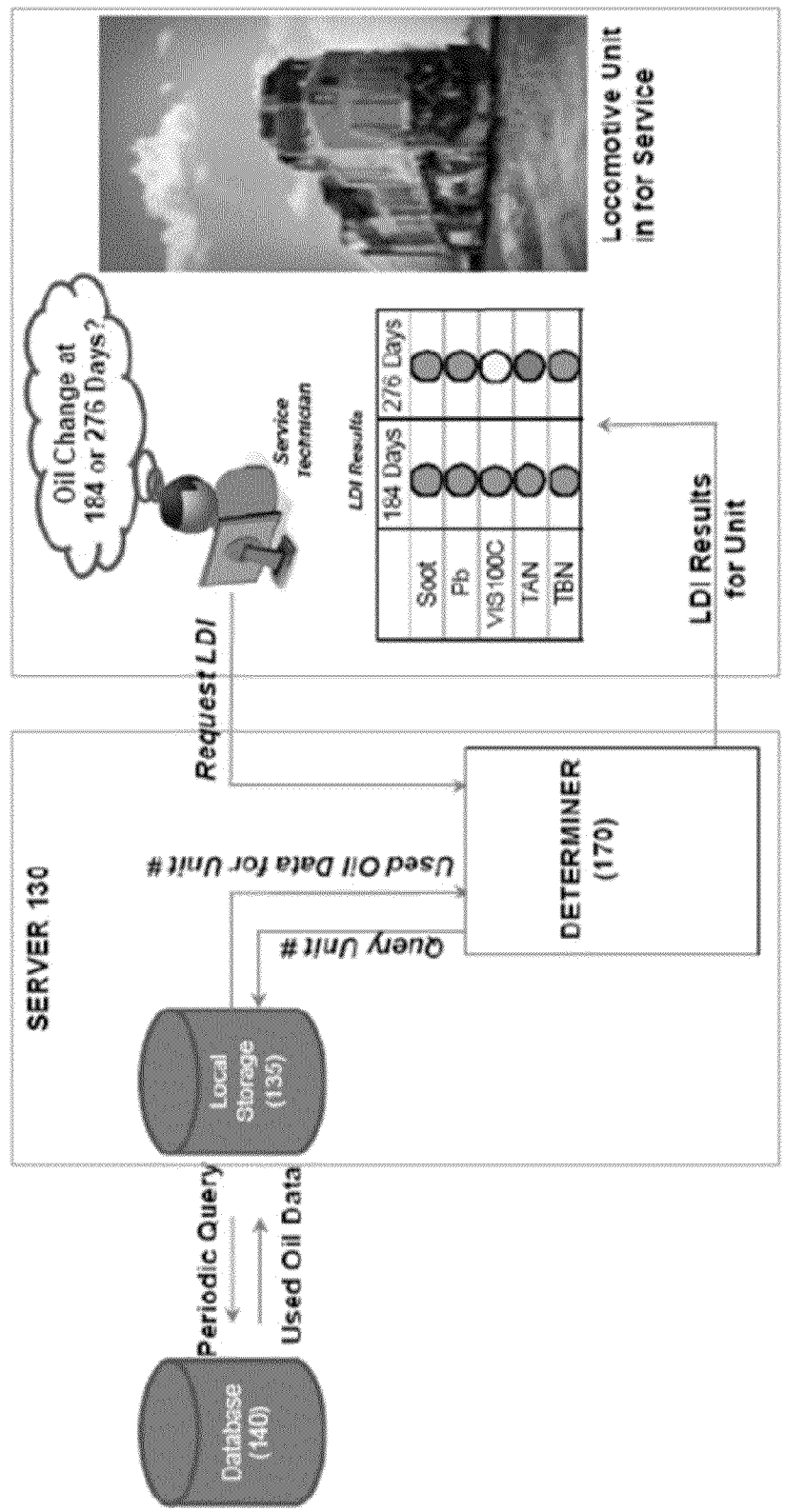
FIG. 5 shows an example of an implementation of the system of FIG. 2A.

FIG. 5 shows an example of an implementation of the system 100 (shown in FIGS. 2A-2B). In this example, the locomotive unit 2248 may be in the shop for its scheduled 184 day service. The service technician, using the computer 120, may request an LDI for the unit 2248 to determine whether it is necessary to replace the engine lubricant at the 184 day point, or if the unit 2248 may continue to run for another 92 days without replacing the engine lubricant. In this regard, the server 130 may query its internal data storage 135 (or database 140, where it is provided internal to the server 130) for historical data for the unit 2248. If the historical data is stored in the remote database 140, then the database 140 may be periodically queried to obtain the most up to date information associated with the unit 2248. The determiner 170 may then process the retrieved historical data for the unit 2248 to generate predicted analysis parameter values AP(1), AP(2), AP(3), AP(4), and AP(5) for the set analysis parameters at 276 days, including (1) soot, (2) lead (Pb), (3) viscosity 100C, (4) TAN, and (5) TBN. It is noted that other (additional or alternative) analysis parameters may be set, as one of ordinary skill in the art will recognize, without departing from the scope or spirit of the disclosure. As seen in FIG. 5, the predicted analysis parameter value $AP(3)_{n+1}$ for viscosity 100C may be at an unacceptable level at 276 days, but the predicted value for $AP(3)_{n+1}$ TAN is at an acceptable level, thereby making it necessary to replace the lubricant before the 276 days, preferably at, e.g., 184 days while the unit 2248 is in the shop.

FIG. 6 shows an example of General Electric (GE) OEM recommendations 600 for a GE locomotive engine that may be retrieved from the database 140. As seen, the recommendations 600 include a list of analysis parameters AP, ranging from copper (Cu) to TBN. In this instance, m=24. Each of the analysis parameters AP has an associated "Critical" threshold value $AP_{TH-C}$, an associated "Abnormal" threshold value $AP_{TH-A}$, and an associated "Marginal" threshold value $AP_{TH-M}$. The recommendations 600 also include a "Problems" column that provides a suggested cause if a particular analysis parameter exceeds anyone of the three identified threshold values.

FIG. 7 shows an example of Electro-Motive Diesel (EMD) OEM recommendations 700 for an EMD locomotive engine that may be retrieved from the database 140. As seen, the recommendations 700 include a list of analysis parameters AP similar to those in FIG. 6, ranging from silver (Ag) to TBN. In this instance, m=25. As discussed earlier with regard to the recommendations 600, each of the analysis parameters in the recommendations 700 has an associated "Critical" threshold value $AP_{TH-C}$, an associated "Abnormal" threshold value $AP_{TH-A}$, and an associated "Marginal" threshold value $AP_{TH-M}$. Like the recommendations 600, the recommendations 700 also include a "Problem" column that suggests causes when a particular analysis parameter is beyond anyone of the three identified threshold values.

In the recommendations 600 (or 700), should a particular analysis parameter go beyond (exceed or be less than) the recommended "Marginal" threshold value, but have a value less extreme than the "Abnormal" threshold value, then the recommendations recommend that the unit (or engine) be "shopped" during the next inspection and the indicated problem (in the "Problem" column) be investigated. If the particular analysis parameter is beyond (exceed or be less than) the recommended "Abnormal" threshold value, but does not go beyond (exceed or be less than) the "Critical" threshold value, then the recommendations recommend that the particular unit (or engine) be sent to the shop immediately for service, and that the associated problem in the "Problem" column be investigated. If the particular analysis parameter goes beyond (exceed or be less than) the recommended "Critical" threshold value, then the recommendations recommend that the particular unit (or engine) be shut down immediately and the unit be serviced, beginning with an investigation of the associated problem identified in the "Problem" column.

FIG. 8 shows an example of historical data 400 that may be retrieved from the database 140 for a particular engine (e.g., locomotive unit 2248), where n=25 and m=1. In this example, the historical data may include four columns of data, including: a TAKEN column that includes the dates on which a lubricant sample was taken from the unit 2248; a TESTED column that includes the respective dates on which the taken lubricant samples were tested; a UNIT column that identifies the engine (e.g., unit 2248); and an analysis parameter column that identifies a particular analysis parameter (Fe), the wear metal iron, and includes n analysis parameter values, from the earliest recorded value, $AP(1)_1=2$ (ppm), to the last recorded value, $AP(1)_{25}=4$ (ppm). As seen, the values $AP(1)_1 \ldots AP(1)_{25}$ range from a low of 2 (ppm) to a high of 18 (ppm).

FIG. 9 shows an example of eight scatter plot charts that may be generated by the server 130 for the iron (Fe) versus oil-age for the locomotive unit 2248. Specifically, the scatter plot charts include seven charts (1 to 7) that show iron concentrations in the engine oil measured at various times for seven past lubricant discard intervals (LDI), and one chart (8) that includes AP(Fe) values for iron for the current LDI interval. As seen in the charts, the iron levels Fe versus oil-age tend to be linear. Thus, when oil changes have been identified, then the oil age can be calculated.

Figure 10:
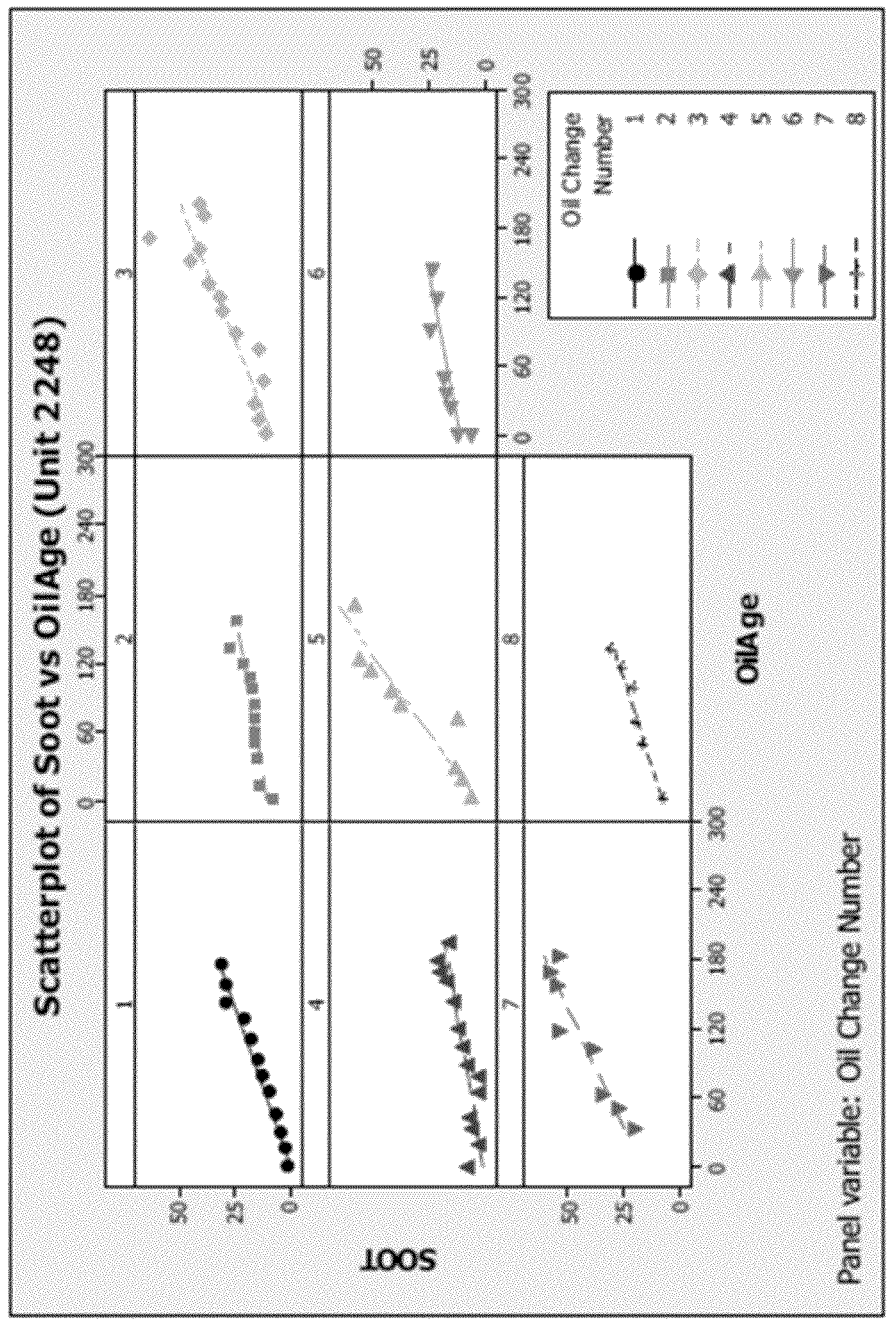
FIG. 10 shows an example of eight scatter plot charts of soot versus oil-age for a locomotive unit.

FIG. 10 shows an example of eight scatter plot charts of soot versus oil-age for the locomotive unit 2248. Specifically, the scatter plot charts include seven charts (1 to 7) that show soot concentrations in the engine oil measured at various times for seven past lubricant discard intervals (LDI), and one chart (8) that includes soot values for the current LDI interval. As seen in the charts, soot levels appear to also be an indicator of oil-age. The data indicates a linear relationship between oil age and soot.

Figure 11:
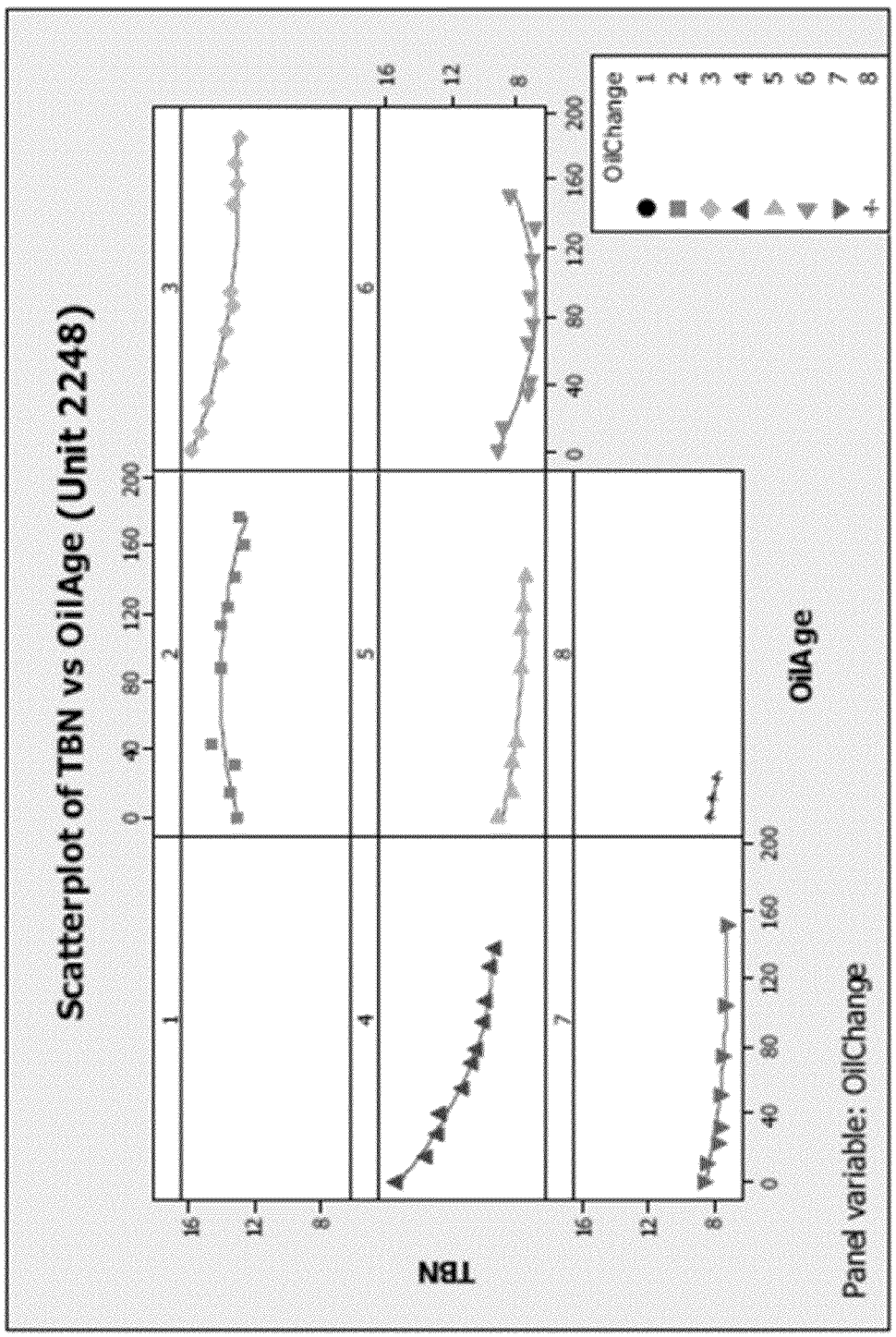
FIG. 11 shows an example of eight scatter plot charts of TBN versus oil-age for a locomotive unit.

FIG. 11 shows an example of eight scatter plot charts of TBN versus oil-age for the locomotive unit 2248. Specifically, the scatter plot charts include six charts (2 to 7) that show TBN levels in the engine oil measured at various times for six past lubricant discard intervals (LDI), one chart (1) for which no historical data is available, and one chart (8) that includes TBN levels for the current period. As seen in the charts, the relationship between oil age and TBN levels may be linear and/or non-linear.

Figure 12:
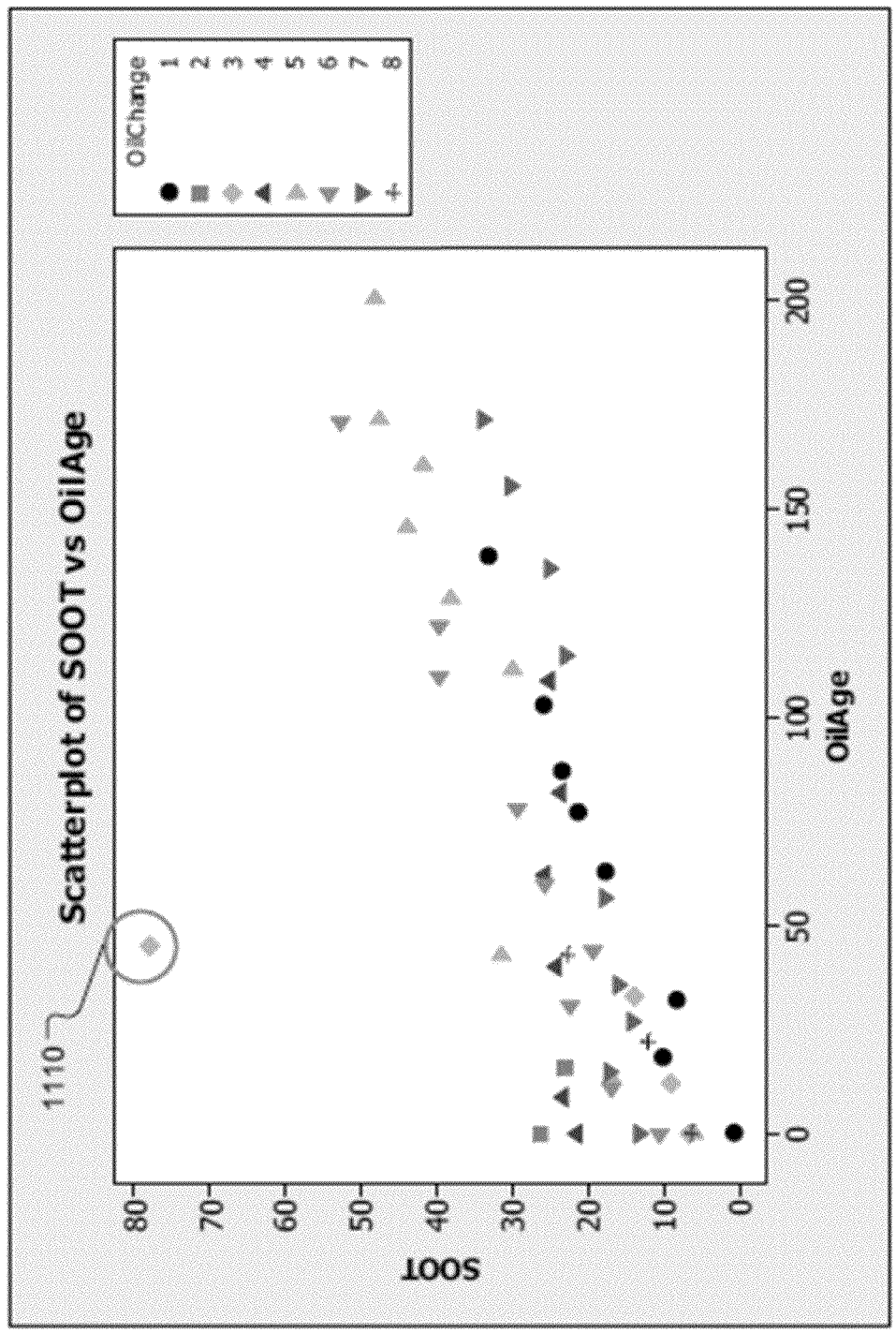
FIG. 12 shows an example of a scatter plot chart of soot versus oil-age for a locomotive unit.

FIG. 12 shows an example of a scatter plot chart of soot versus oil-age for a locomotive unit, with the data for seven (1 to 7) oil change intervals superimposed along with the soot level data during the current oil change interval (8). As seen in the chart, a data point 1110 appears to be an outlier or unusual result data. According to principles of the disclosure, the system 100 (shown in FIGS. 2A-2B) is configured to detect and filter out outlier data, such as, e.g., the data point 1110.

Figure 13:
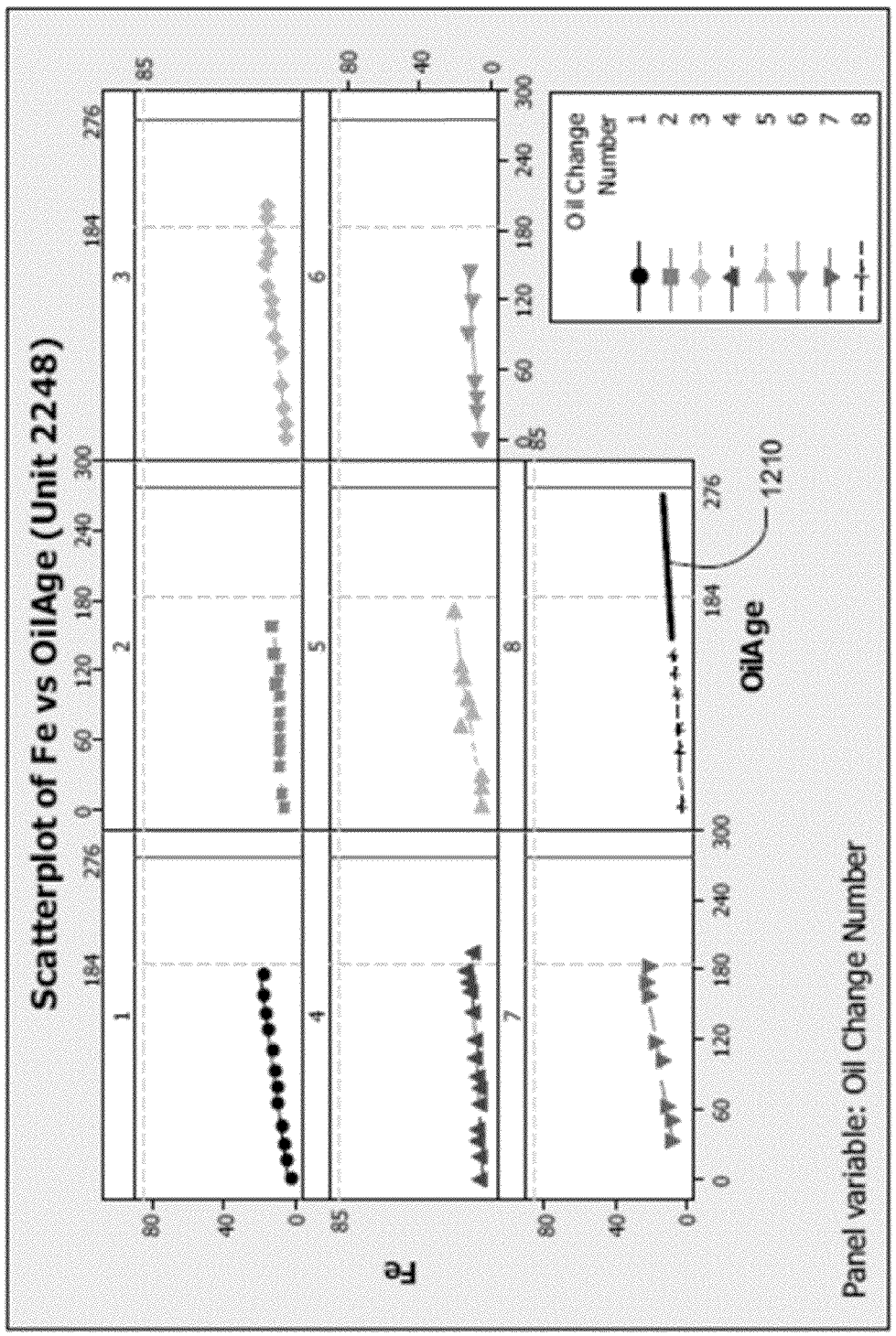
FIG. 13 shows an example of eight scatter plot charts of iron (Fe) versus oil-age for a locomotive unit.

FIG. 13 shows an example of eight scatter plot charts of iron (Fe) versus oil-age for the locomotive unit 2248. FIG. 13 is similar to FIG. 9, except that FIG. 13 further includes a predictor line 1210 that predicts the Fe levels in the engine oil during the period from about 140 days to about 276 days, where the predictor line 1210 may be generated by the determiner 170.

Figure 14:
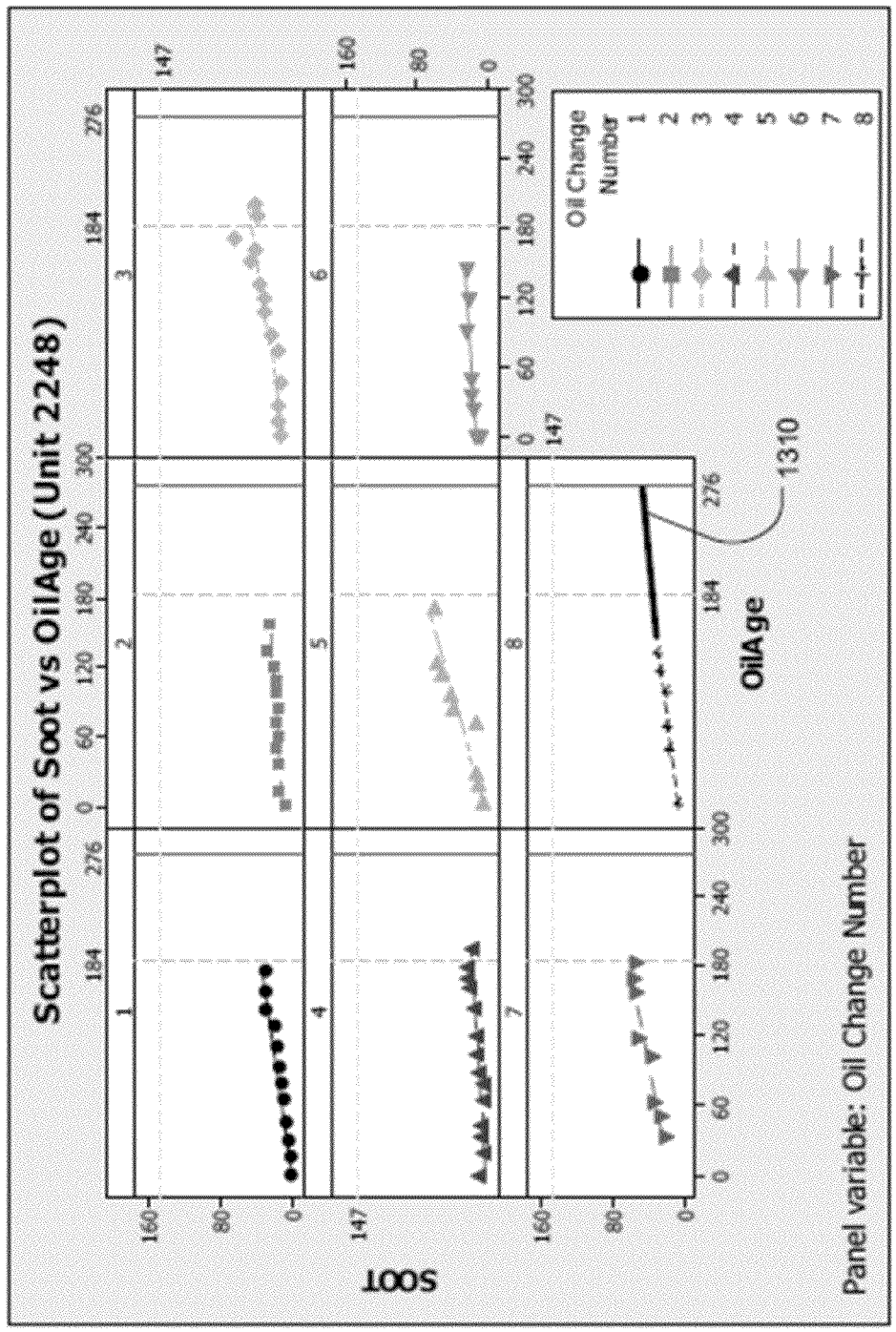
FIG. 14 shows an example of eight scatter plot charts of soot versus oil-age for a locomotive unit.

FIG. 14 shows an example of eight scatter plot charts of soot versus oil-age for the locomotive unit 2248. FIG. 14 is similar to FIG. 10, except that FIG. 14 further includes a predictor line 1310 that predicts the soot levels in the engine oil during the period from about 140 days to about 276 days, where the predictor line 1310 may be generated by the determiner 170.

Figure 15:
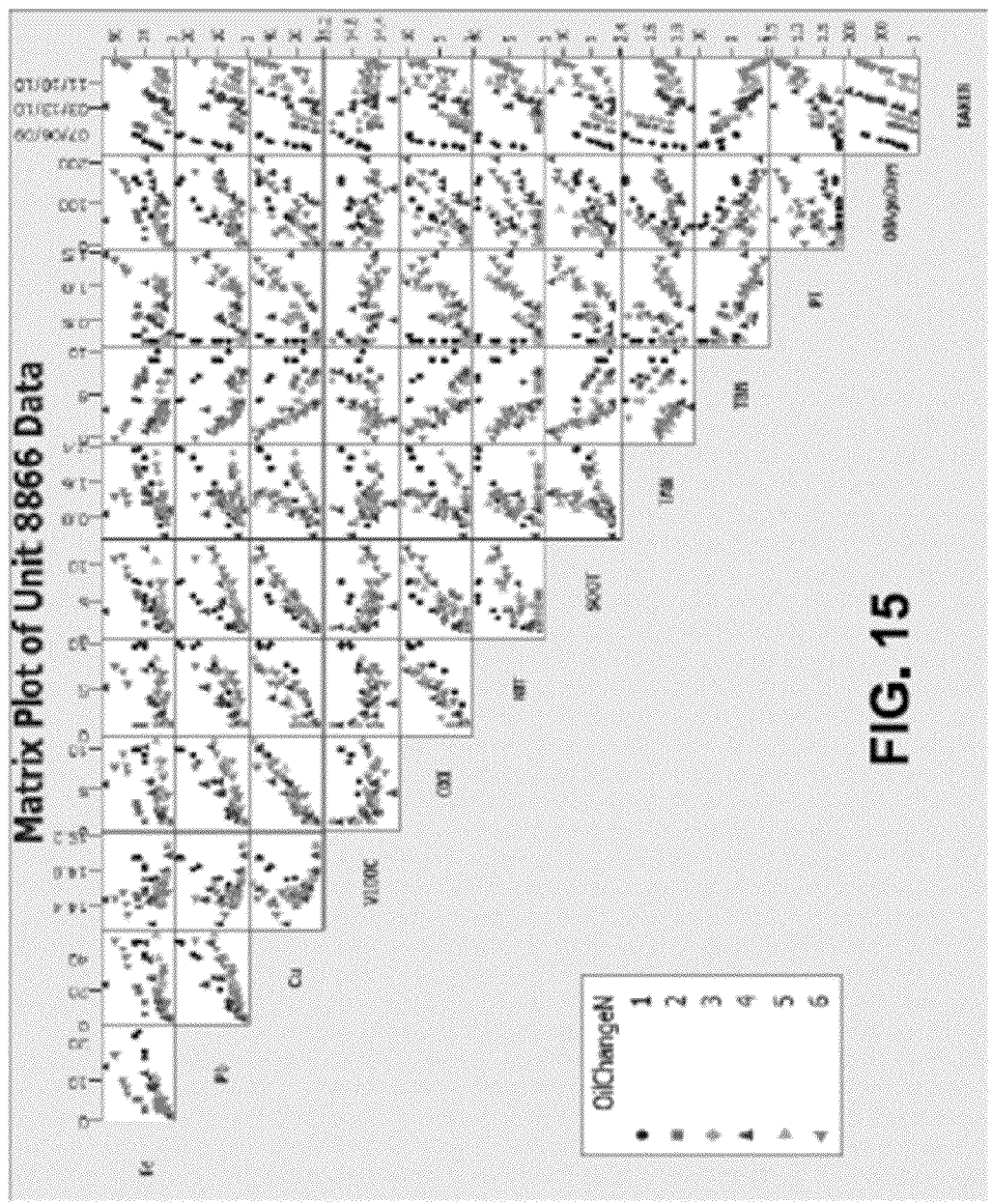
FIG. 15 shows an example of a matrix scatter plot chart for another locomotive unit.

FIG. 15 shows an example of a matrix scatter plot chart for another locomotive unit 8866. As seen in the chart, ten analysis parameters, including Fe, Pb, Cu, V100C, OXI, NIT, SOOT, TAN, TBN, PI, are measured and plotted for six separate oil changes, n=6.

Figure 16:
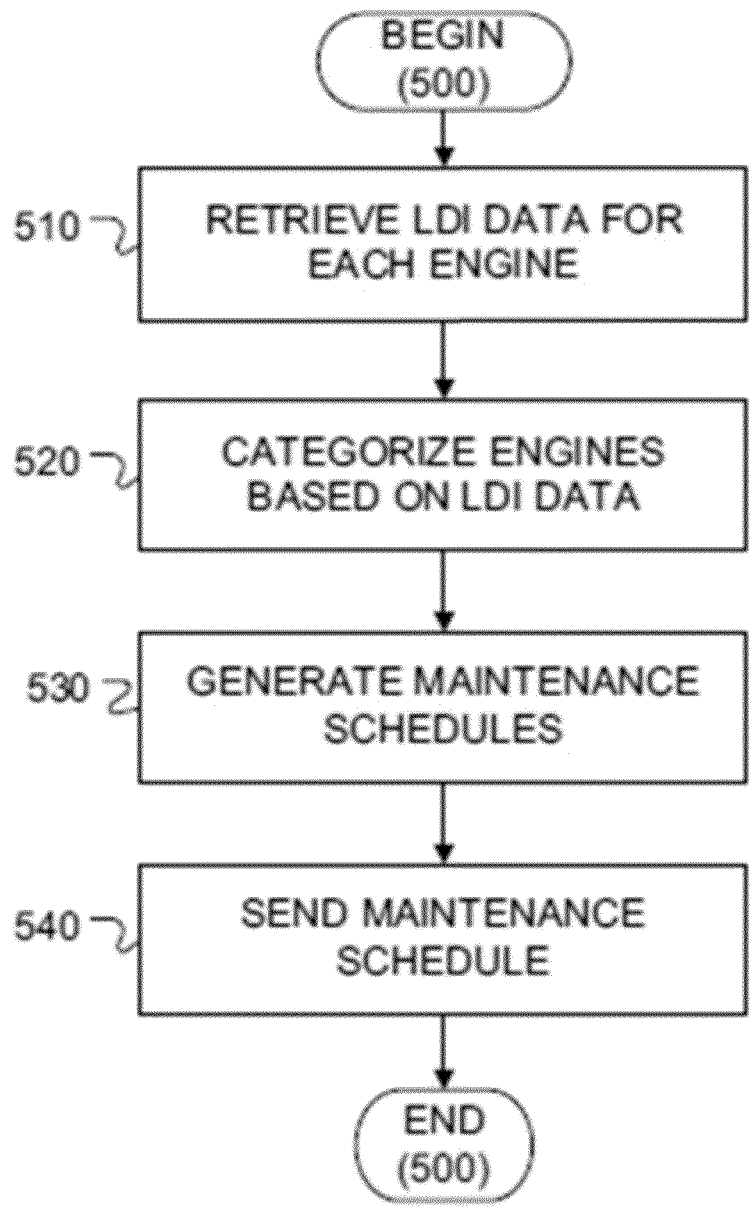
FIG. 16 shows an example of a process for setting a maintenance schedule for one or more engines.

FIG. 16 shows an example of a process 500 for setting a maintenance schedule for one or more engines. Referring to FIG. 2A, the database 140 may be queried to retrieve the LDI data for all (or less than all) of the engines that belong to a particular customer (Step 510). The engines identified in the retrieved data may then be categorized based on the LDI data into one or more LDI categories—e.g., engines that require maintenance every 92 days, engines that require maintenance every 184 days, engines that require maintenance every 276 days, and the like (Step 520). A maintenance schedule may be generated (or updated) for each of the identified engines (Step 530). The maintenance schedule may include a listing of engines that are selected for extended lubricant discard intervals (e.g., LDI=276 days). The maintenance schedule may include a listing of engines that are selected for shortened lubricant discard intervals (e.g., LDI=92 days). The maintenance schedule may include a calendar that identifies the scheduled LDI date for each of the identified engines. The generated maintenance schedule may then be sent to, e.g., the customer computer 120 (Step 540).

According to an aspect of the disclosure, a computer readable medium is provided that contains a computer program, which when executed in, for example, the server 130 (or the computer 120), causes the process 500 in FIG. 16 to be carried out. The computer program may be tangibly embodied in the computer readable medium, which may comprise a code segment or a code section for each of the steps 510 through 540.

The following examples provide illustration of the uses of the system and methods described herein to determine a drain interval for an engine. The examples are for illustrative purposes only and are not intended to limit the scope of the claimed invention.

EXAMPLE 1

Figure 17:
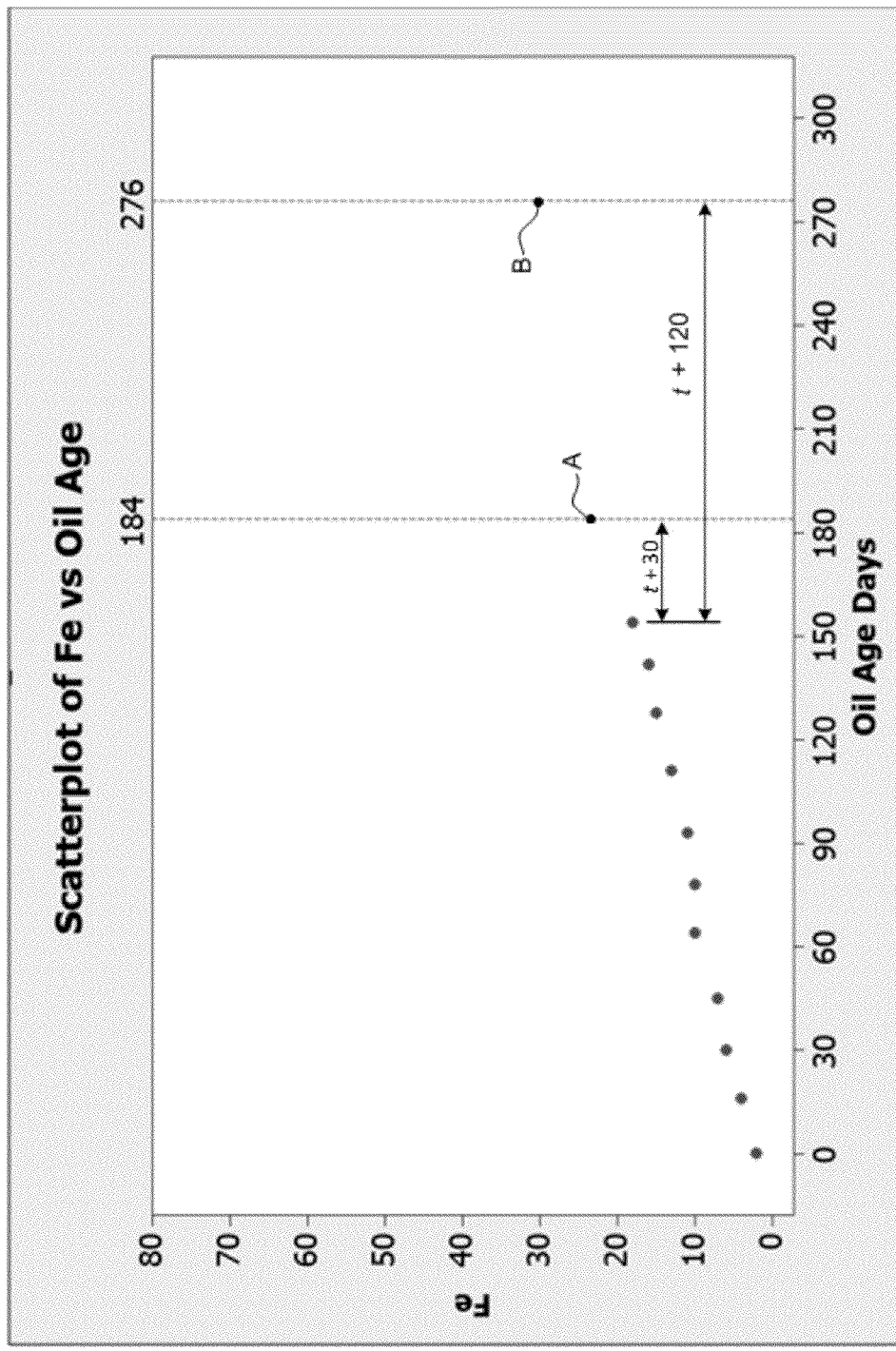
FIG. 17 is a scatter plot for iron versus oil age with predicted values of iron at 184 days and at 276 days.

In the following example a partial least squares analysis of data was used to determine when an analysis parameter value would be expected to exceed a threshold value. In the examples, t+X days are arbitrarily selected to illustrate how the analysis is conducted using the claimed system and methods. In the following tables, the values are of each parameter are determined by t+120 days by interpolating between existing data points for each of the measured parameters in a historical record for an engine. For example, Table 1 shows the interpolated values for iron for a particular engine at t+120 days, where t is the estimated oil age in days. Because there is some lag time between when a sample is obtained and the analysis of the sample is determined, the samples are not collected on the last day of a service interval. In other words, the analysis must be received before a selected service interval so that a decision can be made by the time the service interval date arrives. An example of the decision lag time of t=30 days is illustrated in FIG. 17.

TABLE 1

| Sample No. | Date | Ln(UnitAgeDays + 1) | OilAgeDays (t) | Fe ppmw | Interpolated Fe @ t + 30 Days ppmw | Interpolated Fe @ t + 120 Days ppmw |
|---|---|---|---|---|---|---|
| 1 | 07-22-04 | 4.65 | 0 | 5 | 7.86 | 16.57 |
| 2 | 09-23-04 | 5.12 | 63 | 11 | 14.59 | 20.76 |
| 3 | 10-12-04 | 5.23 | 82 | 13 | 15.99 | 21.88 |
| 4 | 10-15-04 | 5.25 | 85 | 13 | 16.21 | 22.06 |
| 5 | 10-15-04 | 5.25 | 85 | 14 | 16.21 | 22.06 |
| 6 | 12-22-04 | 5.55 | 153 | 19 | 20.76 | 27.89 |
| 7 | 03-17-05 | 5.84 | 238 | 24 | 27.33 | |
| 8 | 04-22-05 | 5.94 | 274 | 28 | | |
| 9 | 08-06-05 | 6.18 | 0 | 7 | 9.00 | 17.52 |
| 10 | 08-28-05 | 6.23 | 22 | 9 | 8.54 | 19.08 |
| 11 | 09-11-05 | 6.26 | 36 | 9 | 8.14 | 22.00 |
| 12 | 10-16-05 | 6.32 | 71 | 8 | 15.09 | 19.41 |
| 13 | 10-28-05 | 6.34 | 83 | 14 | 17.83 | 20.95 |
| 14 | 11-12-05 | 6.37 | 98 | 14 | 17.17 | 22.87 |
| 15 | 11-23-05 | 6.39 | 109 | 18 | 18.46 | |
| 16 | 12-16-05 | 6.42 | 132 | 17 | 19.64 | |
| 17 | 01-09-06 | 6.46 | 156 | 22 | 18.77 | |
| 18 | 01-11-06 | 6.47 | 158 | 20 | 19.03 | |
| 19 | 02-02-06 | 6.50 | 180 | 18 | 21.85 | |
| 20 | 03-13-06 | 6.56 | 219 | 23 | | |
| 21 | 02-15-06 | 6.52 | 0 | 6 | 7.55 | 16.83 |
| 22 | 03-01-06 | 6.54 | 14 | 6 | 9.46 | 17.00 |
| 23 | 03-14-06 | 6.56 | 27 | 7 | 10.55 | 18.47 |
| 24 | 03-25-06 | 6.57 | 38 | 9 | 11.55 | 19.26 |
| 25 | 04-07-06 | 6.59 | 51 | 10 | 12.00 | 19.74 |
| 26 | 04-18-06 | 6.61 | 62 | 11 | 12.00 | 20.30 |
| 27 | 04-29-06 | 6.62 | 73 | 12 | 14.13 | 21.11 |
| 28 | 05-10-06 | 6.64 | 84 | 12 | 16.33 | 21.93 |
| 29 | 05-21-06 | 6.65 | 95 | 12 | 17.00 | 24.18 |
| 30 | 06-05-06 | 6.67 | 110 | 16 | 17.53 | |
| 31 | 06-17-06 | 6.68 | 122 | 17 | 19.04 | |
| 32 | 07-01-06 | 6.70 | 136 | 17 | 19.56 | |
| 33 | 07-16-06 | 6.72 | 151 | 19 | 20.22 | |
| 34 | 08-12-06 | 6.75 | 178 | 20 | 22.65 | |
| 35 | 09-08-06 | 6.78 | 205 | 22 | | |
| 36 | 09-19-06 | 6.80 | 216 | 24 | | |
| 37 | 08-28-06 | 6.77 | 0 | 7 | 10.00 | 13.70 |
| 38 | 09-10-06 | 6.79 | 13 | 11 | 10.20 | 15.67 |
| 39 | 09-23-06 | 6.80 | 26 | 10 | 10.72 | 16.00 |
| 40 | 10-05-06 | 6.81 | 38 | 10 | 11.20 | 16.00 |
| 41 | 12-19-06 | 6.89 | 113 | 13 | 16.00 | |
| 42 | 12-29-06 | 6.90 | 123 | 14 | 16.00 | |
| 43 | 01-10-07 | 6.91 | 135 | 16 | 16.00 | |
| 44 | 02-23-07 | 6.96 | 179 | 16 | | |
| 45 | 09-30-07 | 7.15 | 0 | 5 | 6.88 | 15.50 |
| 46 | 11-17-07 | 7.18 | 48 | 8 | 10.33 | 14.93 |
| 47 | 11-29-07 | 7.19 | 60 | 7 | 11.53 | 18.00 |
| 48 | 12-11-07 | 7.20 | 72 | 9 | 12.92 | 17.00 |
| 49 | 12-20-07 | 7.21 | 81 | 11 | 15.00 | 16.00 |
| 50 | 01-06-08 | 7.22 | 98 | 12 | 15.94 | 16.00 |
| 51 | 01-19-08 | 7.23 | 111 | 15 | 13.43 | 18.20 |
| 52 | 02-06-08 | 7.24 | 129 | 16 | 14.29 | |
| 53 | 02-20-08 | 7.25 | 143 | 13 | 16.09 | |
| 54 | 03-03-08 | 7.26 | 155 | 14 | 17.58 | |
| 55 | 03-17-08 | 7.27 | 169 | 15 | 16.22 | |
| 56 | 03-28-08 | 7.28 | 180 | 18 | 16.00 | |
| 57 | 04-09-08 | 7.29 | 192 | 17 | 16.40 | |
| 58 | 04-18-08 | 7.29 | 201 | 16 | 18.20 | |
| 59 | 05-07-08 | 7.31 | 220 | 16 | | |
| 60 | 05-22-08 | 7.32 | 235 | 19 | | |
| 61 | 05-01-08 | 7.30 | 0 | 5 | 7.00 | 9.81 |
| 62 | 05-13-08 | 7.31 | 12 | 5 | 7.00 | 10.70 |
| 63 | 05-28-08 | 7.32 | 27 | 7 | 7.42 | 11.58 |
| 64 | 06-12-08 | 7.33 | 42 | 7 | 7.83 | 12.58 |
| 65 | 07-18-08 | 7.35 | 78 | 8 | 8.97 | |
| 66 | 08-18-08 | 7.37 | 109 | 9 | 11.16 | |
| 67 | 09-14-08 | 7.39 | 136 | 11 | 12.92 | |
| 68 | 10-03-08 | 7.40 | 155 | 12 | 13.00 | |
| 69 | 10-15-08 | 7.41 | 167 | 13 | | |
| 70 | 11-05-08 | 7.42 | 188 | 13 | | |

As shown in the foregoing table, the expected iron content at t=30 days can be obtained from a data set for Sample Nos. 1 and 2 by linear interpolation between the iron content at t=0 days and the iron content at t=63 days. Likewise, the expected iron content at 120 days can be determined by linear interpolation between Sample Nos. 5 and 6 using the observed iron content for the same data set at t=85 and t=153 days. Based on the foregoing analysis, FIG. 17 is a scatter plot for iron versus oil age with predicted values of iron at 184 days (point A) and at 276 days (point B).

Since the iron content loss rate in the used oil may change over time due to a number of factors such as engine age and interaction with other variables, a partial least squares analysis, regression analysis, or Neural Network analysis, and the like of the interpolated values for each set of data is used to predict the iron content. The same analysis may be conducted for any and/or all selected parameter such as iron, chromium, lead, tin, aluminum, nickel, silver, silicon, boron, sodium, magnesium, calcium barium, phosphorus, zinc, molybdenum, potassium, viscosity at 100° C., oxides, nitrates, sulfides, fuel, water, glycol, soot, total acid number (TAN), total base number (TBN), and the like. The input parameters may also include other non-used oil analysis parameters such as oil pressure, unit/vehicle age, fuel consumption, megawatt hours produced, total miles, total hours, and the like.

EXAMPLE 2

The foregoing analysis can also be done for non-linear data such as viscosity. Table 2 is a table of data for viscosity at 100° C. at t+30 days and t+120 days.

TABLE 2

| Sample No. | Date | Ln(UnitAgeDays + 1) | OilAgeDays (t) | V @ 100° C. | Interpolated V @ 100° C. @ t + 30 Days | Interpolated V @ 100° C. @ t + 120 Days |
|---|---|---|---|---|---|---|
| 1 | 07-22-04 | 4.65 | 0 | 15.3 | 15.62 | 16.54 |
| 2 | 09-23-04 | 5.12 | 63 | 15.97 | 16.17 | 16.89 |
| 3 | 10-12-04 | 5.23 | 82 | 16.21 | 16.43 | 16.83 |
| 4 | 10-15-04 | 5.25 | 85 | 16.23 | 16.47 | 16.82 |
| 5 | 10-15-04 | 5.25 | 85 | 16.06 | 16.47 | 16.82 |
| 6 | 12-22-04 | 5.55 | 153 | 17 | 16.89 | 16.99 |
| 7 | 03-17-05 | 5.84 | 238 | 16.7 | 16.95 | |
| 8 | 04-22-05 | 5.94 | 274 | 17 | | |
| 9 | 08-06-05 | 6.18 | 0 | 15.24 | 15.53 | 16.63 |
| 10 | 08-28-05 | 6.23 | 22 | 15.35 | 15.63 | 16.94 |
| 11 | 09-11-05 | 6.26 | 36 | 15.66 | 15.61 | 16.93 |
| 12 | 10-16-05 | 6.32 | 71 | 15.6 | 16.26 | 17.32 |
| 13 | 10-28-05 | 6.34 | 83 | 16.08 | 16.45 | 17.65 |
| 14 | 11-12-05 | 6.37 | 98 | 16.23 | 16.84 | 18.07 |
| 15 | 11-23-05 | 6.39 | 109 | 16.34 | 16.94 | |
| 16 | 12-16-05 | 6.42 | 132 | 16.95 | 17.35 | |
| 17 | 01-09-06 | 6.46 | 156 | 16.93 | 17.18 | |
| 18 | 01-11-06 | 6.47 | 158 | 17.42 | 17.23 | |
| 19 | 02-02-06 | 6.50 | 180 | 17.01 | 17.85 | |
| 20 | 03-13-06 | 6.56 | 219 | 18.1 | | |
| 21 | 02-15-06 | 6.52 | 0 | 15.28 | 15.43 | 16.91 |
| 22 | 03-01-06 | 6.54 | 14 | 15.32 | 15.71 | 17.16 |
| 23 | 03-14-06 | 6.56 | 27 | 15.37 | 15.90 | 17.43 |
| 24 | 03-25-06 | 6.57 | 38 | 15.59 | 16.04 | 17.54 |
| 25 | 04-07-06 | 6.59 | 51 | 15.86 | 16.21 | 17.58 |
| 26 | 04-18-06 | 6.61 | 62 | 15.93 | 16.37 | 17.66 |
| 27 | 04-29-06 | 6.62 | 73 | 16.14 | 16.61 | 17.82 |
| 28 | 05-10-06 | 6.64 | 84 | 16.23 | 16.83 | 17.99 |
| 29 | 05-21-06 | 6.65 | 95 | 16.42 | 16.99 | 18.18 |
| 30 | 06-05-06 | 6.67 | 110 | 16.78 | 17.29 | |
| 31 | 06-17-06 | 6.68 | 122 | 16.93 | 17.52 | |
| 32 | 07-01-06 | 6.70 | 136 | 17.2 | 17.56 | |
| 33 | 07-16-06 | 6.72 | 151 | 17.52 | 17.64 | |
| 34 | 08-12-06 | 6.75 | 178 | 17.6 | 18.05 | |
| 35 | 09-08-06 | 6.78 | 205 | 18 | | |
| 36 | 09-19-06 | 6.80 | 216 | 18.2 | | |

TABLE 2-continued

| | | | | | | |
|---|---|---|---|---|---|---|
| 37 | 08-28-06 | 6.77 | 0 | 15.24 | 15.38 | 16.17 |
| 38 | 09-10-06 | 6.79 | 13 | 15.37 | 15.53 | 16.29 |
| 39 | 09-23-06 | 6.80 | 26 | 15.32 | 15.64 | 16.40 |
| 40 | 10-05-06 | 6.81 | 38 | 15.49 | 15.74 | 16.49 |
| 41 | 12-19-06 | 6.89 | 113 | 16.12 | 16.37 | |
| 42 | 12-29-06 | 6.90 | 123 | 16.19 | 16.45 | |
| 43 | 01-10-07 | 6.91 | 135 | 16.31 | 16.54 | |
| 44 | 02-23-07 | 6.96 | 179 | 16.65 | | |
| 45 | 09-30-07 | 7.15 | 0 | 15.09 | 15.25 | 16.14 |
| 46 | 11-17-07 | 7.18 | 48 | 15.35 | 14.96 | 17.00 |
| 47 | 11-29-07 | 7.19 | 60 | 15.36 | 15.28 | 17.49 |
| 48 | 12-11-07 | 7.20 | 72 | 15.13 | 15.76 | 17.46 |
| 49 | 12-20-07 | 7.21 | 81 | 14.88 | 16.06 | 17.45 |
| 50 | 01-06-08 | 7.22 | 98 | 15.63 | 16.20 | 17.58 |
| 51 | 01-19-08 | 7.23 | 111 | 16.06 | 16.33 | 17.83 |
| 52 | 02-06-08 | 7.24 | 129 | 16.21 | 17.25 | |
| 53 | 02-20-08 | 7.25 | 143 | 16.35 | 17.16 | |
| 54 | 03-03-08 | 7.26 | 155 | 17.36 | 17.48 | |
| 55 | 03-17-08 | 7.27 | 169 | 16.97 | 17.45 | |
| 56 | 03-28-08 | 7.28 | 180 | 17.49 | 17.52 | |
| 57 | 04-09-08 | 7.29 | 192 | 17.46 | 17.64 | |
| 58 | 04-18-08 | 7.29 | 201 | 17.45 | 17.83 | |
| 59 | 05-07-08 | 7.31 | 220 | 17.6 | | |
| 60 | 05-22-08 | 7.32 | 235 | 17.91 | | |
| 61 | 05-01-08 | 7.30 | 0 | 15.22 | 15.39 | 15.96 |
| 62 | 05-13-08 | 7.31 | 12 | 15.24 | 15.52 | 16.04 |
| 63 | 05-28-08 | 7.32 | 27 | 15.36 | 15.60 | 16.31 |
| 64 | 06-12-08 | 7.33 | 42 | 15.52 | 15.67 | 16.58 |
| 65 | 07-18-08 | 7.35 | 78 | 15.7 | 15.88 | 16.70 |
| 66 | 08-18-08 | 7.37 | 109 | 15.89 | 16.14 | 17.00 |
| 67 | 09-14-08 | 7.39 | 136 | 16.07 | 16.63 | 17.15 |
| 68 | 10-03-08 | 7.40 | 155 | 16.49 | 16.61 | |
| 69 | 10-15-08 | 7.41 | 167 | 16.64 | 16.69 | |
| 70 | 11-05-08 | 7.42 | 188 | 16.6 | 16.90 | |
| 71 | 12-02-08 | 7.44 | 215 | 16.87 | | |
| 72 | 12-17-08 | 7.45 | 230 | 17.01 | | |
| 73 | 01-11-09 | 7.46 | 255 | 17.14 | | |

Figure 18:
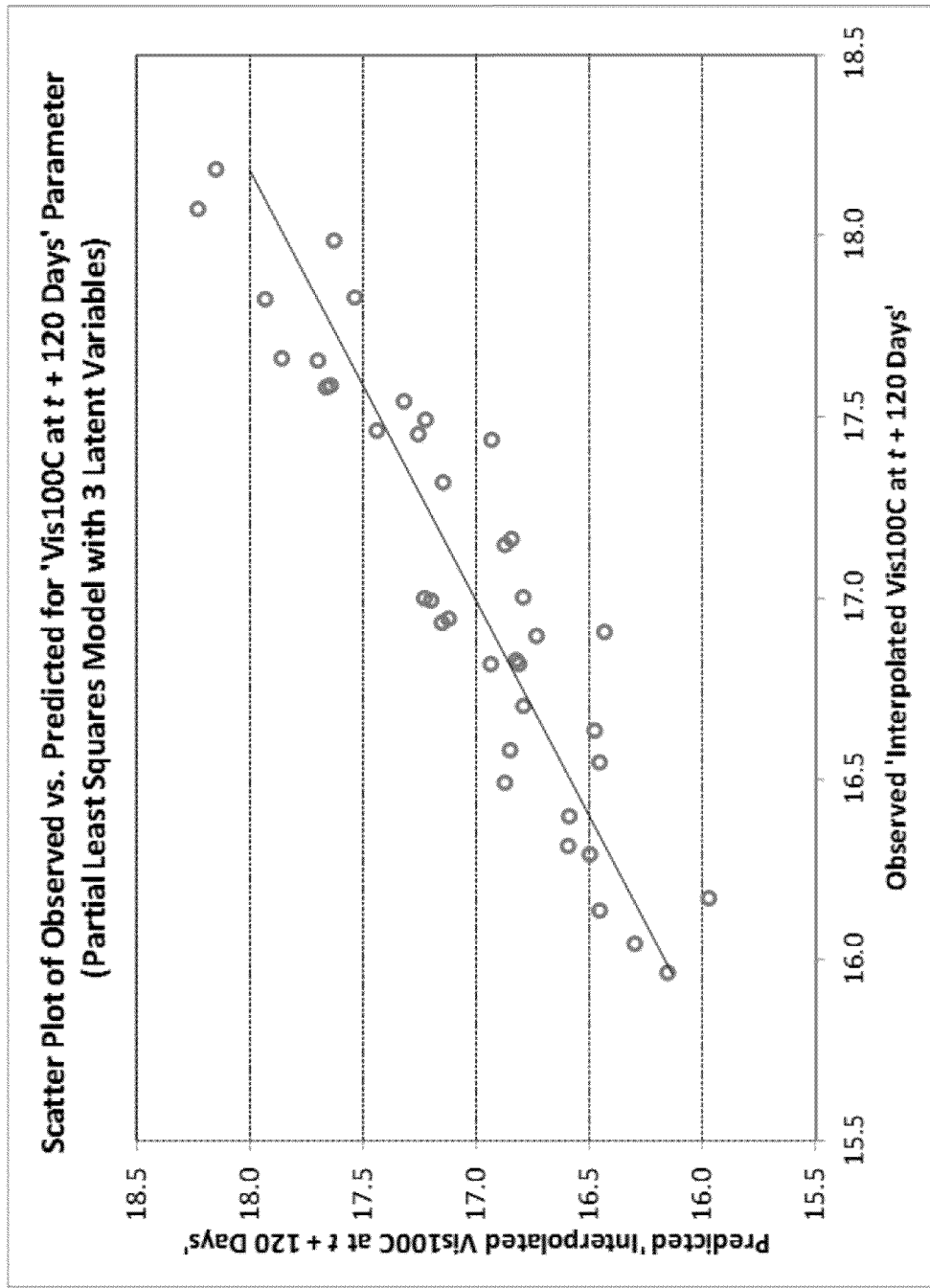
FIG. 18 is a scatter plot for predicted viscosity at 100° C. according to one embodiment of the disclosure.
Figure 19:
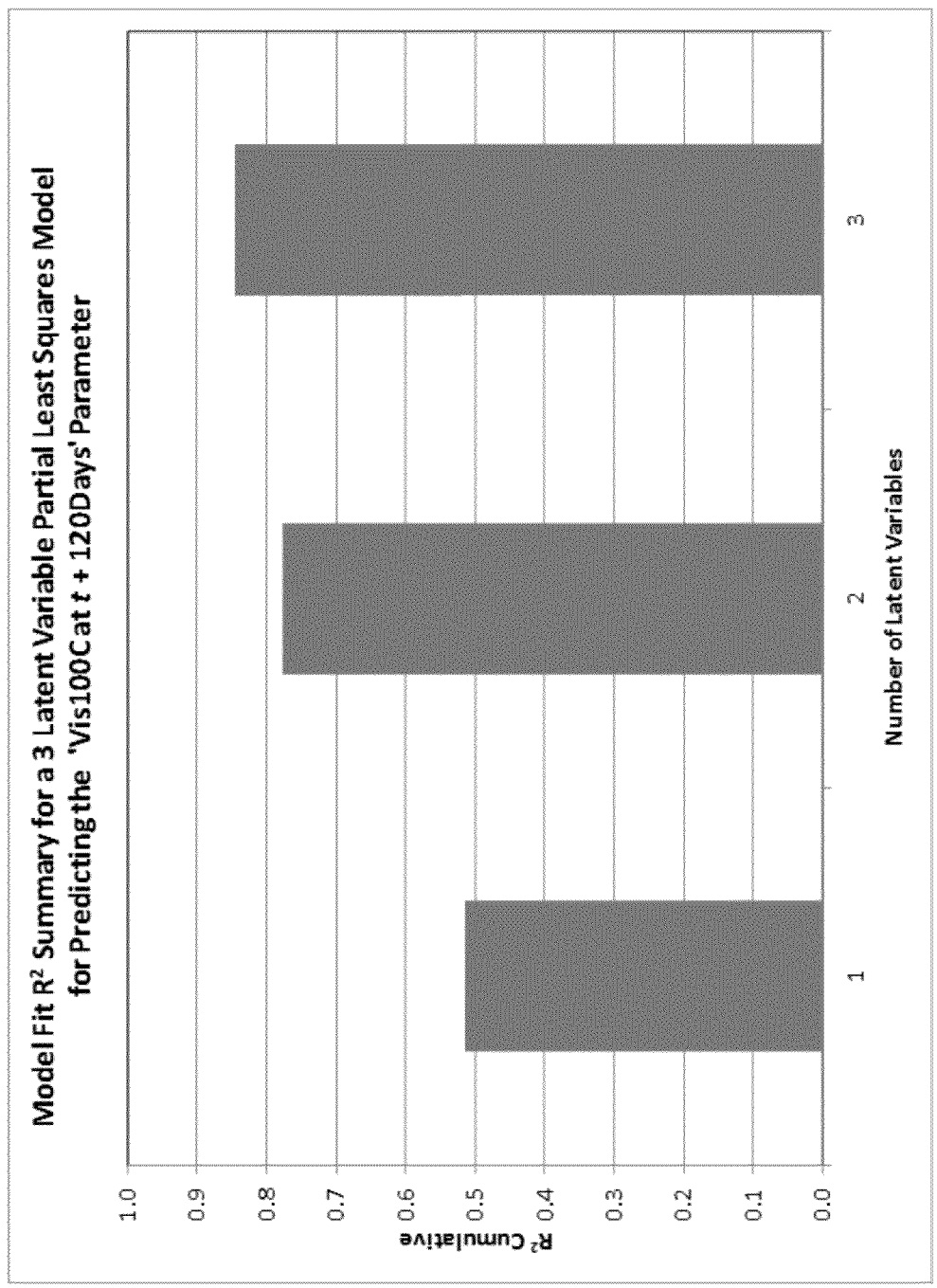
FIG. 19 is a graphical representation of a partial least squares model fit with three latent variables according to the embodiment of the disclosure depicted in FIG. 17.
Figure 20:
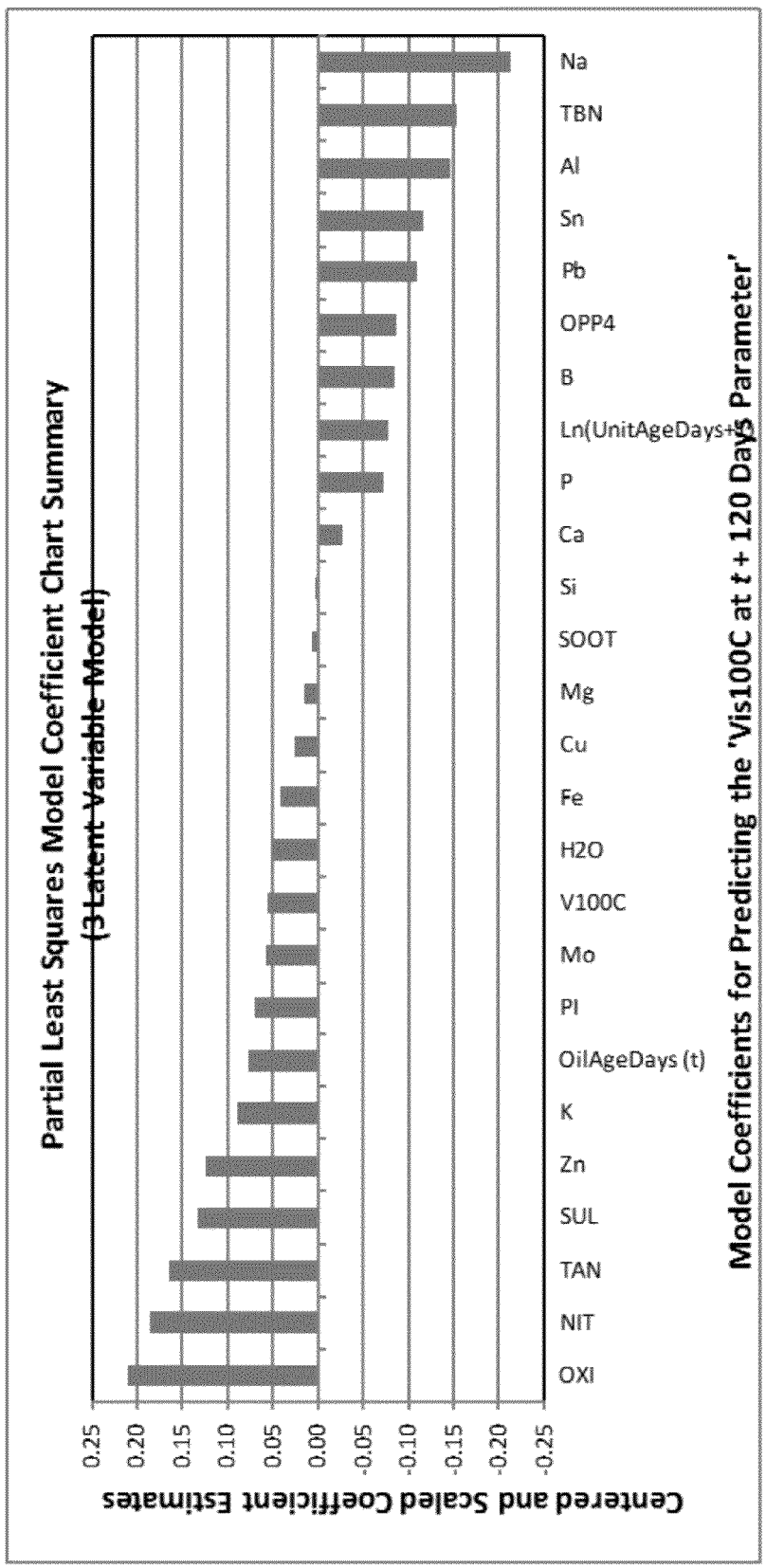
FIG. 20 is a coefficient chart for the three latent variables depicted in FIG. 19.
Figure 21:
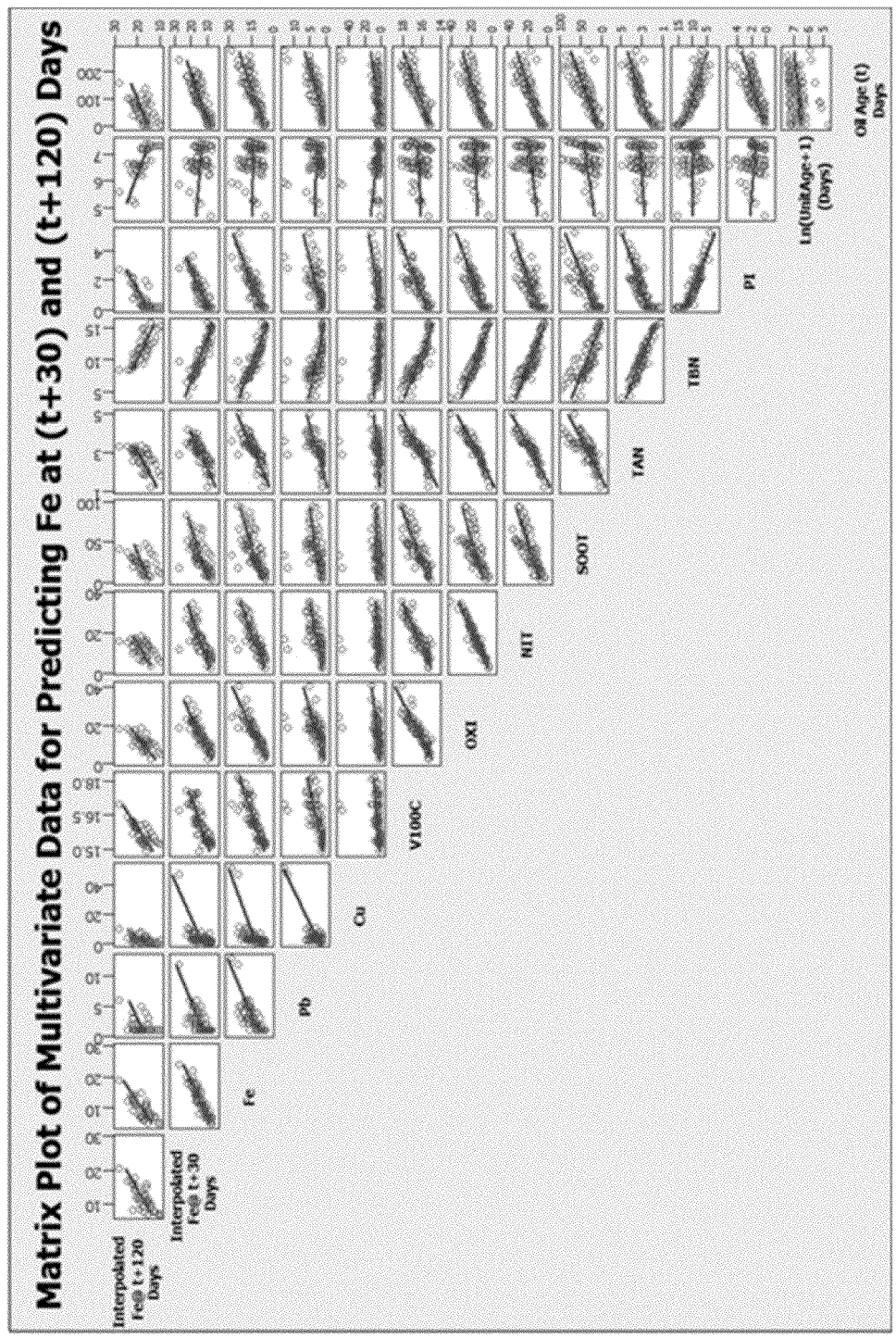
FIG. 21 is a matrix plot of multivariate data for predicting iron content in oil at r+30 days and at t+120 days.
Figure 22:
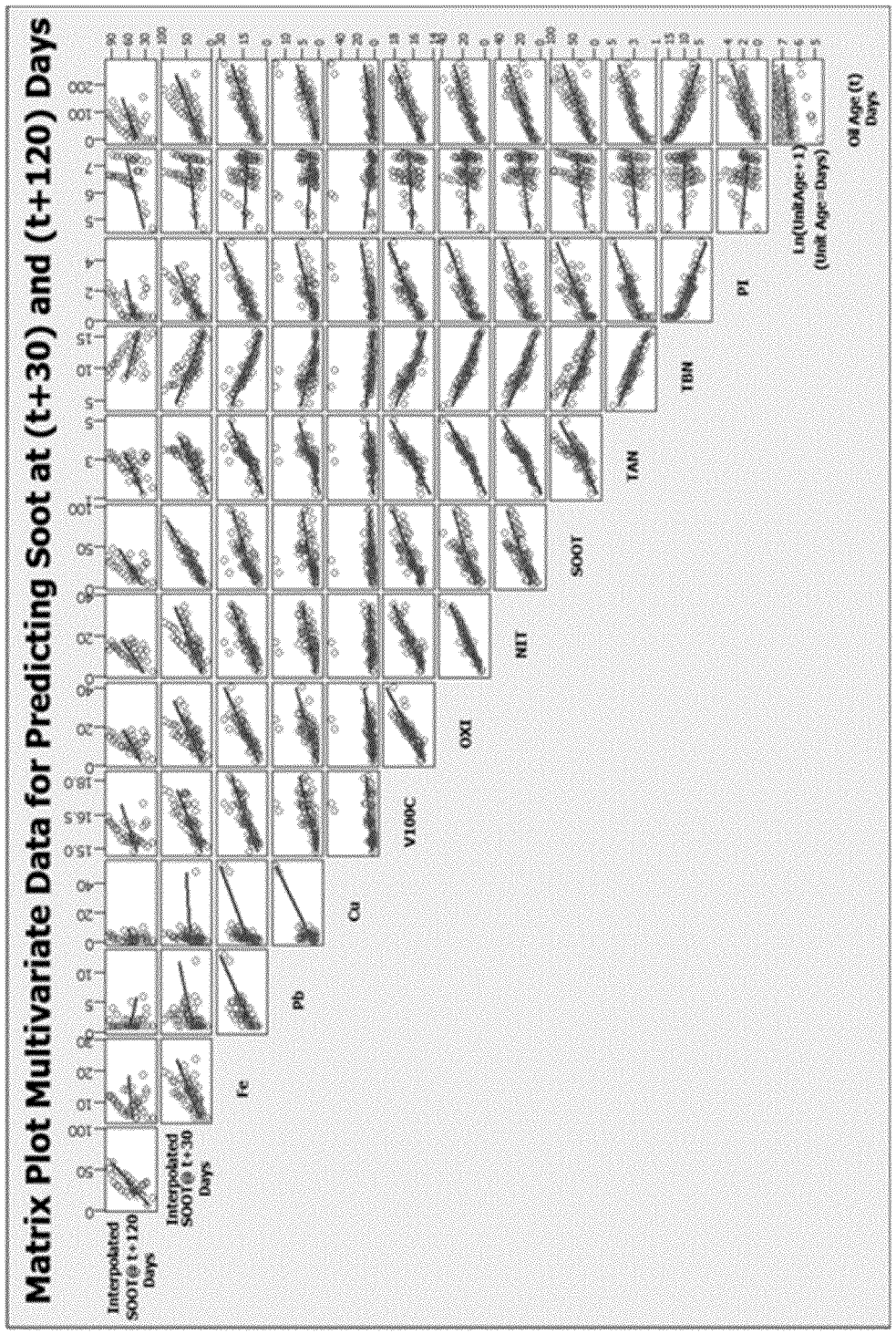
FIG. 22 is a matrix plot of multivariate data for predicting soot content in oil at t+30 days and at t+120 days.

FIG. 18 is a scatter plot of observed versus predicted value of viscosity at 100° C. at t+120 days using a partial least squares model with a 3 latent variable model. FIG. 19 is a graphical representation of the amount of variation explained for a 3 latent variable model using the partial least squares model for predicting the viscosity at 100° C. at t+120 days for the data. FIG. 20 is a partial least squares model coefficient chart summary of the three latent variable model depicted in FIG. 19 showing the relative importance/effects of various parameter used for predicting the viscosity at 100° C. at t+120 days. FIGS. 21 and 22 are scatter plots of the multivariate data that was analyzed to predict the interpolated iron content and soot content at t+30 and t+120 days in the oil. The matrix plots also illustrate the multicollinear relationships of the interpolated t+30 and t+120 iron and soot content output parameters with respect to the multiple analysis input parameters.

Figure 23:
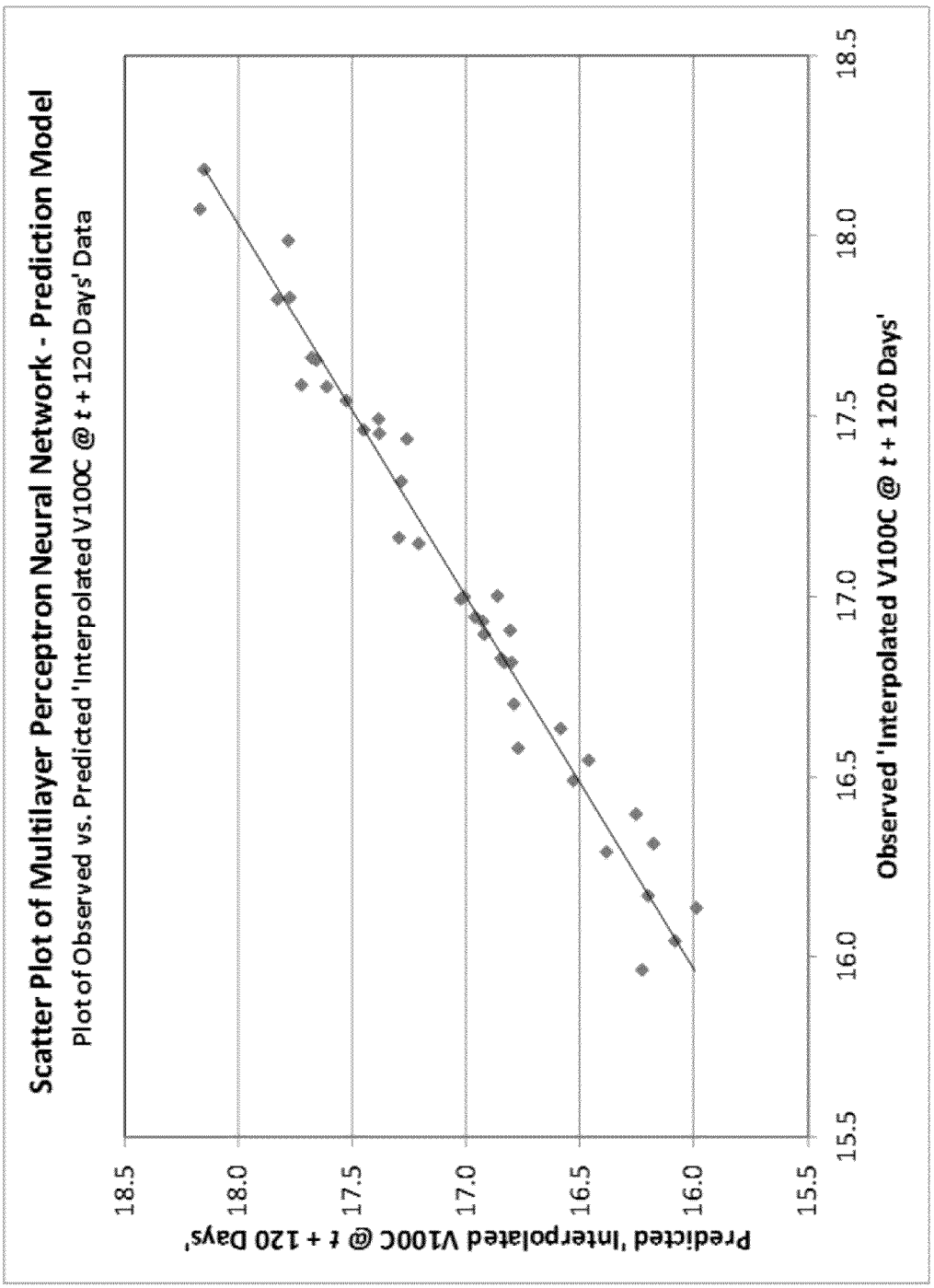
FIG. 23 is a scatter plot for predicted viscosity at 100° C. according to a second embodiment of the disclosure.

FIG. 23 is a scatter plot of viscosity data at 100° C. (KV100) for a multilayer perceptron neural network prediction model showing observed versus predicted interpolated viscosity data at 100° C. at t+120 days. Multiple analysis input parameters were selected to develop the 'Interpolated 100° C. Viscosity at t+120 days' Neural Network prediction model.

According to a further aspect of the disclosure, a marker may be added to the lubricant. The marker may produce a measurable change once the lubricant becomes spent. The marker may be measurable by, e.g., visible spectrum analysis, infrared analysis, color change, or the like.

While the disclosure has been described in terms of exemplary embodiments, those skilled in the art will recognize that the disclosure can be practiced with modifications in the spirit and scope of the appended claims. These examples are merely illustrative and are not meant to be an exhaustive list of all possible designs, embodiments, applications or modifications of the disclosure.

What is claimed:

1. A processor-based system for predicting a lubricant drain interval in an engine based on a plurality of analysis parameter values measured in a plurality of samples of used engine lubricant taken from the engine over a period of time, the system comprising:

a first input that receives the plurality of analysis parameter values and a plurality of historical analysis parameter values for the engine that are indicative of one or more characteristics of the used lubricant and stores the plurality of analysis parameter values and historical analysis parameter values in a memory of a processor;

a second input that receives an analysis parameter threshold value for the used lubricant at the end of a service interval and stores the analysis parameter threshold value in a memory of the processor;

a determiner that determines a future analysis parameter value for determining the lubricant drain interval by performing modeling of the plurality of analysis parameter values and the historical analysis parameter values, and comparing the future analysis parameter value to the analysis parameter threshold value to determine whether or not the future analysis parameter value exceeds the analysis parameter threshold value at the end of the service interval in order to provide an output indicating the lubricant drain interval (LDI) in an engine, wherein the modeling performed by the determiner is selected from a partial least squares regression model and a neural network model, and wherein said analysis parameter values and said historical analysis parameter values comprise three or more used lubricant analysis parameters, and said analysis parameter values and said historical analysis parameter values further comprise two or more non used lubricant analysis parameters.

2. The system of claim 1, wherein the determiner is configured to generate the lubricant drain interval for the engine.

3. The system of claim 1, wherein the engine lubricant comprises a crankcase engine oil.

4. The system of claim 1, wherein said determiner comprises a computer that predicts the lubricant drain interval.

5. The system of claim 4, wherein the computer comprises the determiner.

6. The system of claim 1, wherein said used lubricant analysis parameters comprise three or more parameters selected from a group consisting of iron, lead, tin, copper aluminum, boron, oxidation, nitration, potassium, silicon, sodium, soot, TBN, water, fuel, sludge, and insolubles in the engine lubricant sample.

7. The system of claim 1, wherein the used lubricant analysis parameters comprise three or more parameters selected from a group of analysis parameters consisting of zinc, boron, oxidation, nitration, potassium, silicon, sodium, soot, water, fuel contaminant, fuel byproducts, sludge, lead, and insolubles.

8. The system of claim 7, wherein the non used lubricant analysis parameters comprise at least two or more of non used lubricant analysis parameters selected from the group consisting of oil pressure, run time hours of an engine or unit, engine temperature, megawatt hours produced, total miles of the unit or engine between oil changes, and age of the engine or unit.

9. A processor-based method for predicting a lubricant drain interval in an engine based on a plurality of analysis parameter values measured in a sample of used engine lubricant taken from the engine, the method comprising:
receiving at a first input of a processor the plurality of analysis parameter values and a plurality of historical analysis parameter values for the engine that are indicative of one or more characteristics of the used lubricant and storing the plurality of analysis parameter values and historical analysis parameter values in a memory of the processor;
receiving at a second input of the processor an analysis parameter threshold value for the used lubricant at the end of a service interval and storing the analysis parameter threshold value in the memory of the processor; and
using the processor (a) to determine a future analysis parameter value for the used lubricant by performing modeling of the plurality of analysis parameter values and the historical analysis parameter values; (b) to compare the future analysis parameter value and the analysis parameter threshold value to determine whether the future analysis parameter value exceeds the analysis parameter threshold value at the end of the service interval; and (c) to provide an output indicating the lubricant drain interval (LDI), wherein the modeling performed by the processor is selected from a partial least squares regression model and a neural network model, and wherein said analysis parameter values and said historical analysis parameter values comprise three or more used lubricant analysis parameters, and said analysis parameter values and said historical analysis parameter values further comprise two or more non used lubricant analysis parameters selected from the group consisting of oil pressure, run time hours of an engine or unit, engine temperature, megawatt hours produced, total miles of the unit or engine between oil changes, and age of the engine or unit.

10. The method of claim 9, further comprising:
predicting the service interval for the used lubricant.

11. The method of claim 9, wherein the engine is provided in one or more of: a tractor; a locomotive; a bus; an automobile; a motorcycle; a scooter; a watercraft; an aircraft; a truck; a wind turbine; or a generator.

* * * * *